United States Patent [19]
Igari et al.

[11] Patent Number: 6,087,324
[45] Date of Patent: Jul. 11, 2000

[54] SUSTAINED-RELEASE PREPARATION

[75] Inventors: Yasutaka Igari; Yutaka Yamagata, both of Kobe, Japan

[73] Assignee: Takeda Chemical Industries, Ltd., Osaka, Japan

[21] Appl. No.: 08/644,631

[22] Filed: Apr. 22, 1996

Related U.S. Application Data

[63] Continuation-in-part of application No. PCT/JP95/01771, Sep. 6, 1995, abandoned, and a continuation-in-part of application No. 08/265,124, Jun. 24, 1994, abandoned.

[30] Foreign Application Priority Data

| Jun. 24, 1993 | [JP] | Japan | 5-153393 |
| Sep. 9, 1994 | [JP] | Japan | 6-216449 |
| Dec. 14, 1994 | [JP] | Japan | 6-310291 |

[51] Int. Cl.$^7$ ................................. A61K 28/18
[52] U.S. Cl. ................... 514/2; 424/499; 514/3; 514/12; 530/399
[58] Field of Search ............... 514/3, 2, 12; 424/499; 530/399

[56] References Cited

U.S. PATENT DOCUMENTS

| 4,853,218 | 8/1989 | Yim et al. ............................ 424/85.7 |
| 5,114,918 | 5/1992 | Ishikawa et al. .................... 514/11 |
| 5,192,741 | 3/1993 | Orsolini et al. ..................... 514/4 |
| 5,270,313 | 12/1993 | Burri et al. ......................... 514/252 |
| 5,271,945 | 12/1993 | Yoshioka et al. ................... 424/489 |
| 5,284,828 | 2/1994 | Hemmi et al. ...................... 514/18 |
| 5,292,740 | 3/1994 | Burri et al. ......................... 514/256 |
| 5,445,832 | 8/1995 | Orsolini et al. ..................... 424/491 |
| 5,510,331 | 4/1996 | Hamon et al. ...................... 514/13 |
| 5,643,607 | 7/1997 | Okada et al. ....................... 514/3 |
| 5,654,010 | 8/1997 | Johnson et al. ..................... 424/502 |
| 5,711,968 | 1/1998 | Tracy et al. ......................... 424/487 |

FOREIGN PATENT DOCUMENTS

| 0 052 510 | 5/1982 | European Pat. Off. . |
| 0 216 485 | 4/1987 | European Pat. Off. . |
| 0 251 476 | 1/1988 | European Pat. Off. . |
| 0 350 246 | 1/1990 | European Pat. Off. . |
| 0 467 389 | 1/1992 | European Pat. Off. . |
| 0467389 | 1/1992 | European Pat. Off. . |
| 0 528 312 | 2/1993 | European Pat. Off. . |
| 0 601 799 | 6/1994 | European Pat. Off. . |
| 2257909 | 1/1993 | United Kingdom . |
| 92/17200 | 10/1992 | WIPO . |
| 93/08799 | 5/1993 | WIPO . |
| 93/10144 | 5/1993 | WIPO . |
| 93/17668 | 9/1993 | WIPO . |
| 94/12158 | 6/1994 | WIPO . |

OTHER PUBLICATIONS

Patent Abstract of JP 4–288099.

Lam et al., "Cochinmicins, Novel and Potent Cyclodepsipeptide Endothelin Antagonists from *A Microbisphora sp.* I. Production, Isolation and Characterization", The Journal of Antibiotics, vol. 45, No. 11, pp. 1709–1716, May 1992.

Zink et al., "Cochinmicins, Novel and Potent Cyclodepsipeptide Endothelin Antagonists from *A Microbispora sp.* II. Structure Determination", The Journal of Antibiotics, vol. 45, No. 11, pp. 1717–1722, May 1992.

U.S. Patent application No. 071 984,323 of Henry Auer, et al., Controlled Released Growth Hormone Containing Microspheres, Filed Dec. 2, 1992.

*Primary Examiner*—Peter O'Sullivan
*Attorney, Agent, or Firm*—Foley & Lardner

[57] ABSTRACT

According to a first embodiment, there is provided a sustained-release preparation comprising a water-insoluble or slightly water-soluble polyvalent metal salt of a water-soluble physiologically active substance which is not an endothelin antagonist, and a biodegradable polymer. The sustained-release preparation of the first embodiment is highly efficient in incorporating the water-soluble physiologically active substance and suppresses the initial burst of the water-soluble physiologically active substance. The sustained-release preparation of the present invention is capable of releasing the water-soluble physiologically active substance while retaining its bioactivity after administration in vivo. Furthermore, the water-soluble physiologically active substance in the sustained-release preparation is kept stable for a long period of time, with little loss of bioactivity.

According to a second embodiment, there is provided a sustained-release preparation comprising an anti-endothelin substance and a biodegradable polymer. The sustained-release preparation of the present invention sustainedly releases an anti-endothelin substance, serving well in the treatment of endothelin-associated diseases.

23 Claims, 1 Drawing Sheet

DRAWINGS

SUSTAINED-RELEASE PREPARATION

This application is a continuation-in-part of PCT/JP95/01771 filed Sep. 6, 1995, now abandoned, and a continuation-in-part of application Ser. No. 08/265,124 filed Jun. 24, 1994 now abandoned.

The following disclosure through page 31 relates to a first embodiment of the present invention.

TECHNICAL FIELD OF THE FIRST EMBODIMENT

The first embodiment of the present invention relates to a sustained-release preparation which comprises a water-insoluble or a slightly water-soluble polyvalent metal salt of a water-soluble peptide type of physiologically active substance which is not an endothelin antagonist, and a biodegradable polymer.

BACKGROUND ART OF THE FIRST EMBODIMENT

Physiologically active substances, particularly peptides or derivatives thereof, are known to exhibit various pharmacologic actions in vivo. Some have been produced in large amounts, for pharmaceutical application, by chemical synthesis, or as a result of advances in gene engineering and cell engineering technologies, using organisms such as *Escherichia coli,* yeasts, animal cells and hamsters. However, these peptides must be administered frequently, since they generally have a short biological half-life, and so pose a significant physical burden of injection on patents. To solve this problem, various attempts have been made to develop sustained-release preparations.

The first problem to solve in developing a sustained-release preparation of a water-soluble physiologically active substance, particularly a water-soluble peptide (hereinafter also referred to as "peptide") is to control peptide solubility, i.e., to regulate the peptide release rate.

Japanese Publication of the Translation of International Patent Application No. 500286/1991 discloses an insoluble zinc-protamine-α-interferon complex.

Japanese Patent Unexamined Publication No. 2930/1988 discloses a system comprising a polylactide in which a macromolecular polypeptide is dispersed.

Japanese Patent Unexamined Publication Nos. 221855/1993 and 172208/1994 disclose a technology by which a water-soluble peptide is converted to a water-insoluble peptide salt, which is then suspended in an organic medium containing a biodegradable polymer to efficiently incorporate the water-soluble peptide in fine grains. The water-insoluble peptide used in these patent publications is an organic acid salt formed at the base portion of the water-soluble peptide molecule, and is exemplified by pamoate, tannic acid, stearic acid or palmitate.

Although there have been various attempts to produce sustained-release preparations of water-soluble physiologically active substances, as stated above, no satisfactory sustained-release preparations have been obtained; there is therefore need for the development of a sustained-release preparation that is highly efficient in incorporating water-soluble physiologically active substance, suppresses initial water-soluble physiologically active substance burst, offers a constant water-soluble physiologically active substance release rate, and keeps the bioactivity of water-soluble physiologically active substance.

DISCLOSURE OF THE FIRST EMBODIMENT

Through extensive investigation to solve the above problems, the present inventors found that a sustained-release preparation, having dramatically increased efficiency of water-soluble peptide type of physiologically active substance except for an endothelin antagonist incorporation in a biodegradable polymer and showing little drug burst just after administration to the living body, can be obtained by producing a water-insoluble or a slightly water-soluble polyvalent metal salt of a water-soluble peptide type of physiologically active substance except for an endothelin antagonist (hereinafter also referred to as "complex"), which salt is formed from a combination of a water-soluble peptide type of physiologically active substance except for an endothelin antagonist having an acidic group, or a water-soluble salt thereof (hereinafter also referred to as "physiologically active substance"), with a water-soluble polyvalent metal salt, and dispersing or dissolving it in a biodegradable polymer. After further investigations based on this finding, the inventors developed the present invention.

Accordingly, the present invention relates to:

(1) a sustained-release preparation which comprises
  (a) a water-insoluble or slightly water-soluble polyvalent metal salt of a water-soluble peptide type of physiologically active substance except for an endothelin antagonist and
  (b) a biodegradable polymer,
(2) a preparation of term 1 above, wherein the physiologically active substance is a water-soluble peptide or a derivative thereof,
(3) a preparation of term 2 above, wherein the peptide is a hormone, cytokine, hematopoietic factor, growth factor, enzyme, soluble or solubilized receptor, antibody, antigen containing peptide, blood coagulation factor or adhesion molecule,
(4) a preparation of term 2 above, wherein the peptide is a hormone,
(5) a preparation of term 4 above, wherein the hormone is a growth hormone
(6) a preparation of term 3 above, wherein the hormone is an insulin,
(7) a preparation of term 2 above, wherein the peptide is a cytokine,
(8) a preparation of term 7 above, wherein the cytokine is an interferon,
(9) a preparation of term 2 above, wherein the peptide is a growth factor,
(10) a preparation of term 1 above, wherein the polyvalent metal salt is a transition metal salt,
(11) a preparation of term 1 above, wherein the polyvalent metal salt is a zinc salt,
(12) a preparation of term 1 above, wherein the solubility of the polyvalent metal salt to water is about 0 to about 0.1% (w/w) at 20° C.,
(13) a preparation of term 1 above, wherein the solubility of the polyvalent metal salt to water is about 0 to about 0.01% (w/w),
(14) a preparation of term 1 above, which contains about 0.1 to about 50% (w/w) of the polyvalent metal salt,
(15) a preparation of term 1 above, which contains about 1 to about 30% (w/w) of the polyvalent metal salt,
(16) a preparation of term 1 above, wherein the biodegradable polymer is an aliphatic polyester,
(17) a preparation of term 16 above, wherein the aliphatic polyester is a polymer of lactic acid and glycolic acid,
(18) a preparation of term 17 above, wherein the composition ratio of lactic acid and glycolic acid is 100/0 to about 40/60 (mole %),
(19) a preparation of term 18 above, wherein the composition ratio is about 90/10 to about 45/55 (mole %),
(20) a preparation of term 17 above, wherein the weight-average molecular weight of the polymer is about 3,000 to about 20,000,

(21) a preparation of term 17 above, wherein the weight-average molecular weight of the polymer is about 3,000 to about 14,000,

(22) a preparation of term 16 above, wherein the alihatic polyester is a homopolymer of lactic acid,

(23) a preparation of term 22 above, wherein the weight-average molecular weight of the homopolymer is about 3,000 to about 20,000,

(24) a preparation of term 22 above, wherein a weight-average molecular weight of the homopolymer is about 3,000 to about 14,000,

(25) a preparation of term 1 above, wherein the preparation is a microcapsule,

(26) a preparation of term 25 above, wherein the microcapsule is for injection,

(27) a preparation of term 1 above, which is an injectable one,

(28) Use of a water-insoluble or slightly water-soluble polyvalent metal salt of a water-soluble peptide type of physiologically active substance except for an endothelin antagonist and a biodegradable polymer for the production of a sustained-release preparation, and

(29) a method of producing a sustained-release preparation, which comprises dispersing a water-insoluble or slightly water-soluble polyvalent metal salt of a water-soluble peptide type of physiologically active substance except for an endothelin antagonist in an oil phase containing a biodegradable polymer to make a solid-in-oil emulsion, adding the solid-in-oil emulsion to a water phase to make a solid-in-oil-in-water emulsion, and then in-water drying the solid-in-oil-in-water emulsion.

Incidentally abbreviations of amino acid, peptide or the like used in the present invention are based on those in accordance with IUPAC-IUB Commission on Biochemical Nomenclature or those conventionally used in the relevant fields, and possible optical isomers of amino acid are, unless otherwise specified, L-isomers.

The physiologically active substance in the water-insoluble or the slightly water-soluble polyvalent metal salt is a physiologically active substance having an acidic group. Here, the acidic group is exemplified by the carboxyl group and sulfo group. The physiologically active substance is preferably a physiologically active substance having a peptide bond or an amino acid and acidic group. The acidic group may be derived from an amino acid. More preferably, the physiologically active substance is a water-soluble peptide having an acidic group or a derivative thereof. A solubility of the physiologically active substance to water is 1% (w/w) or more at 25° C.

The physiologically active substance preferably has two or more carboxyl groups.

The molecular weight of the physiologically active substance is about 200 to 200,000, preferably about 200 to about 50,000, more preferably about 500 to about 40,000.

A representative activity of a physiologically active substance is hormone action. The physiologically active substance may be a natural, synthetic, semi-synthetic or genetically engineered product, or a derivative thereof. As concerns the mechanism of action, these physiologically active substances may be agonistic or antagonistic.

Physiologically active substances, particularly water-soluble peptide or a derivative thereof for the present invention include hormones, cytokines, hematopoietic factors, growth factors, enzymes, a soluble or solubilized receptor, an antibody or a fragment thereof, an antigen containing peptide, a blood coagulation factor, an adhesion molecule, agonists or antagonists capable of binding to receptors of the physiologically active substances and so on.

Example hormones include insulin, growth hormone, natriuretic peptide, gastrin, prolactin, adrenocortico-tropic hormone (ACTH), thyroid-stimulating hormone (TSH), luteinizing hormone (LH), follicle-stimulating hormone (FSH), human chorionic gonadotropin (HCG), motilin, kallikrein and so on. The hormone is preferably insulin and growth hormone.

Example cytokines include lymphokines, monokines and so on. Example lymphokines include interferons (alpha, beta, gamma), interleukins (IL-2 through IL-12) and so on. Example monokines include an interleukin 1 (IL-1), tumor necrosis factor and so on. The cytokine is preferably a lymphokine, more preferably an interferon (alpha, beta, gamma).

Example hematopoietic factors include erythropoietin, granulocyte colony-stimulating factor (G-CSF), macrophage colony-stimulating factor (M-CSF), thrombopoietin, platelet growth-stimulating factor, megakaryocyte potentiator and so on.

Example growth factors include basic or acidic fibroblast growth factors (FGF), members of the family thereof (e.g., FGF-9 etc.), nerve cell growth factor (NGF) or members of the family thereof, insulin-like growth factors (e.g., IGF-1, IGF-2), bone morphogenetic protein (BMP) or members of the family thereof and so on.

Example enzymes include superoxide dismutase (SOD), tissue plasminogen activator (TPA) and so on.

Example soluble receptors include soluble IL-6 receptor, insulin-like growth factor binding protein (IGFBP), soluble TNF receptor, soluble EGF receptor, soluble IL-1 receptor and so on.

Example solubilized receptors include a known receptors such as IL-1 receptor, IL-6 receptor, TNF receptor or Fas ligand etc., which is solubilized by a method of gene engineering.

Example antibodies include a human monoclonal antibody, a human-mouse chimeric monoclonal antibody in which the variable region of an antibody derived from mouse is bound to the constant region of an antibody derived from human, or a fragment thereof and so on. Example type of antibody include IgM, IgG, IgE and so on. Example antigenes, which is recognized by the above described antibody, include platelet, virus and so on.

Example blood coagulation factors include factor VIII and so on.

Example adhesion molecules include fibronectin, ICAM-1 and so on.

Furthermore, example physiologically active substances include endothelin, Arg—Gly—Asp—Ser (RGDS), pituitary adenylate cyclase activating polypeptide (PACAP) and so on.

The physiologically active substance is converted to a water-insoluble or a slightly water-soluble polyvalent metal salt thereof by bringing it into contact with a water-soluble polyvalent metal salt.

The polyvalent metal in the water-soluble polyvalent metal salt is exemplified by divalent, trivalent or tetravalent metal etc. such as alkaline earth metals (e.g., calcium, magnesium etc.), transition metals [e.g., iron (II, III), copper (II), zinc (II) etc.), the group IIIb metals [e.g., aluminum (II, III) etc.], the group IVb metals [e.g., tin (II, IV) etc.] and so on. The polyvalent metal is preferably alkaline earth metals or transition metals, more preferably calcium or zinc, still more preferably zinc.

Water-soluble polyvalent metal salts include salts of polyvalent metals and acids, e.g., salts of polyvalent metals and inorganic acids, and salts of polyvalent metals and organic acids.

The salt of a polyvalent metal and an acid is preferably a salt whose water solubility at normal temperature (20° C.) is not lower than about 20 mg/ml, more preferably not lower than about 100 mg/ml, and still more preferably not lower than about 200 mg/ml.

Inorganic acids to form salts with polyvalent metals include hydrochloric acid, sulfuric acid, nitric acid, thiocyanic acid and so on.

Organic acids to form salts with polyvalent metals include aliphatic carboxylic acids and aromatic acids. The aliphatic carboxylic acid is preferably an aliphatic carboxylic acid having 2 to 9 carbon atoms. Aliphatic carboxylic acids include aliphatic monocarboxylic acids, aliphatic dicarboxylic acids, aliphatic tricarboxylic acids and so on. These aliphatic carboxylic acids may be saturated or unsaturated one.

Example aliphatic monocarboxylic acids include saturated aliphatic monocarboxylic acids having 2 to 9 carbon atoms (e.g., acetic acid, propionic acid, butyric acid, valeric acid, caproic acid, enanthic acid, caprylic acid, pelargonic acid, caprynic acid etc.) and unsaturated aliphatic monocarboxylic acids having 2 to 9 carbon atoms (e.g., acrylic acid, propiolic acid, methacrylic acid, crotonic acid, isocrotonic acid etc.).

Example aliphatic dicarboxylic acids include saturated aliphatic dicarboxylic acids having 2 to 9 carbon atoms (e.g., malonic acid, succinic acid, glutaric acid, adipic acid, pimelic acid etc.) and unsaturated aliphatic dicarboxylic acids having 2 to 9 carbon atoms (e.g., maleic acid, fumaric acid, citraconic acid, mesaconic acid etc.).

Example aliphatic tricarboxylic acids include saturated aliphatic tricarboxylic acids having 2 to 9 carbon atoms (e.g., tricarballylic acid, 1,2,3-butanetricarboxylic acid etc.).

The above-mentioned aliphatic carboxylic acids may have 1 or 2 hydroxyl groups. Such aliphatic carboxylic acids include glycolic acid, lactic acid, glyceric acid, tartronic acid, malic acid, tartaric acid, citric acid and so on.

The aliphatic carboxylic acid is preferably an aliphatic monocarboxylic acid, more preferably an aliphatic monocarboxylic acid having 2 to 9 carbon atoms, and still more preferably a saturated aliphatic monocarboxylic acid having 2 or 3 carbon atoms. Examples of particularly preferable aliphatic carboxylic acids include acetic acid and so on.

Example aromatic acids include benzoic acid, salicylic acid and so on, with preference given to benzoic acid.

Examples of salts of polyvalent metals and inorganic acids, i.e., inorganic acid polyvalent metal salts, include halides (e.g., zinc chloride, calcium chloride), sulfates, nitrates, thiocyanates and so on.

Examples of salts of polyvalent metals and aliphatic carboxylic acids, i.e., aliphatic carboxylic acid polyvalent metal salts, include calcium acetate, zinc acetate, calcium propionate, zinc glycolate, calcium lactate, zinc lactate, zinc tartrate and so on. Preferable aliphatic carboxylic acid polyvalent metal salts include calcium acetate and zinc acetate. Greater preference is given to zinc acetate.

Examples of salts of polyvalent metals and aromatic acids, i.e., aromatic acid polyvalent metal salts, include benzoates, salicylates and so on. Greater preference is given to zinc benzoate.

A water-insoluble or a slightly water-soluble polyvalent metal salt of a physiologically active substance is produced by mixing in a solvent the water-soluble physiologically active substance and a water-soluble polyvalent metal salt. The mixing procedure is preferably conducted in water.

The mixing ratio (mole ratio) of the physiologically active substance and water-soluble polyvalent metal salt in water is, for example 1:1 to 1:1000, preferably 1:1 to 1:100, more preferably 1:1 to 1:50, still more preferably 1:1 to 1:10. The concentrations of both components in water may be optional, as long as they exceed the solubility of the resulting complex, within their respective solubility ranges.

The pH of the aqueous solution resulting from the above mixing must be such that the bioactivity of the physiologically active substance is not affected, and that the solubilities of the physiologically active substance and water-soluble polyvalent metal salt are not lowered in excess. Although the mixing procedure is normally conducted in distilled water, it may be conducted in water adjusted to weakly acidic, neutral, or weakly alkaline pH as necessary. "Being water insoluble or slightly water-soluble" as mentioned herein is not irreversible but reversible, meaning that water solubility is very low. Water solubility is about 0 to about 0.1% (w/w), preferably about 0 to about 0.01% (w/w) at ordinary temperature (20° C.).

The thus-obtained water insoluble or slightly water-soluble polyvalent metal salt of a water-soluble physiologically active substance is used after being vacuum dried or freeze dried as necessary.

In the sustained-release preparation of the present invention, the content of the water-insoluble or slightly water-soluble polyvalent metal salt of the physiologically active substance is normally about 0.1 to about 50% (w/w), preferably about 1 to about 30% (w/w).

The biodegradable polymer is exemplified by high-molecular polymers slightly soluble or insoluble in water, such as aliphatic polyesters (e.g., homopolymers, copolymers or mixtures thereof synthesized from one or more $\alpha$-hydroxycarboxylic acids such as glycolic acid, lactic acid, hydroxybutyric acid etc.), hydroxydicarboxylic acids such as malic acid etc., hydroxytricarboxylic acids such as citric acid etc. and others, poly-$\alpha$-cyanoacrylic acid esters, polyamino acids such as poly-$\gamma$-benzyl-L-glutamic acid and so on. These may be used in mixture at appropriate ratios. The type of polymerization may be random, block or graft.

The biodegradable polymer is preferably an aliphatic polyester (e.g., a homopolymer, copolymer or mixture thereof synthesized from one or more $\alpha$-hydroxycarboxylic acids such as glycolic acid, lactic acid, hydroxybutyric acid etc., hydroxydicarboxylic acids such as malic acid etc., hydroxytricarboxylic acids such as citric acid etc. and others).

Of the above-mentioned aliphatic polyesters, homopolymers or copolymers synthesized from one or more $\alpha$-hydroxycarboxylic acids (e.g., glycolic acid, lactic acid, hydroxybutyric acid etc.) are preferred from the viewpoint of reliable biodegradability and biocompatibility. More preferably, the aliphatic polyester is a copolymer synthesized from one or more $\alpha$-hydroxycarboxylic acids (e.g., glycolic acid, lactic acid, hydroxybutyric acid etc.). Also, these copolymers may be used in mixture.

The biodegradable polymer for the present invention is produced by a commonly known method.

Although the above-described $\alpha$-hydroxycarboxylic acid may be of the D-, L- or D,L-configuration, it is preferable that the ratio of the D-/L-configuration (mole %) fall within the range from about 75/25 to about 25/75. The ratio of the D-/L-configuration (mole %) is more preferably about 60/40 to about 30/70.

Example copolymers of the above-described $\alpha$-hydroxycarboxylic acid include copolymers of glycolic acid with another $\alpha$-hydroxy acid, which is preferably lactic acid or 2-hydroxybutyric acid.

The $\alpha$-hydroxycarboxylic acid copolymer is preferably a lactic acid-glycolic acid copolymer or a 2-hydroxybutyric acid-glycolic acid copolymer.

More preferably, the α-hydroxycarboxylic acid copolymer is a lactic acid-glycolic acid copolymer.

With respect to the lactic acid-glycolic acid copolymer, it is preferable that the content ratio (lactic acid/glycolic acid) (mole %) be about 100/0 to about 40/60. The content ratio is more preferably about 90/10 to about 45/55, and more preferably about 80/20 to about 45/55. The weight-average molecular weight of the lactic acid-glycolic acid copolymer is about 3,000 to about 20,000, preferably about 3,000 to about 14,000 more preferably about 3,000 to about 12,000.

Also, the degree of dispersion of the lactic acid-glycolic acid copolymer (weight-average molecular weight/number-average molecular weight) is preferably about 1.2 to about 4.0, more preferably about 1.5 to about 3.5.

The lactic acid-glycolic acid copolymer can be synthesized by a known process, such as the method described in Japanese Patent Unexamined Publication No. 28521/1986. It is preferable that the copolymer be synthesized by catalyst-free dehydration polymerization condensation.

With respect to the 2-hydroxybutyric acid-glycolic acid copolymer, it is preferable that glycolic acid account for about 10 to about 75 mole % and 2-hydroxybutyric acid for the remaining portion. More preferably, glycolic acid accounts for about 20 to about 75 mole %, and still more preferably about 30 to about 70 mole %. The weight-average molecular weight of the 2-hydroxybutyric acid-glycolic acid copolymer is preferably about 2,000 to about 20,000. The degree of dispersion of the 2-hydroxybutyric acid-glycolic acid copolymer (weight-average molecular weight/number-average molecular weight) is preferably about 1.2 to 4.0, more preferably about 1.5 to 3.5. A 2-hydroxybutyric acid-glycolic acid copolymer can be synthesized by a known process, such as that described in Japanese Patent Unexamined Publication No. 28521/1986. It is preferable that the copolymer be synthesized by catalyst-free dehydration polymerization condensation.

Preferable example homopolymers of the above-described α-hydroxycarboxylic acid include homopolymer of lactic acid. The weight-average molecular weight of the homopolymer of lactic acid is about 3,000 to about 20,000, preferably about 3,000 to about 14,000. A homopolymer of lactic acid can be synthesized by a known process, such as that described in Japanese Patent Unexamined Publication No. 28521/1986. It is preferable that the homopolymer be synthesized by catalyst-free dehydration polymerization condensation.

The above-described 2-hydroxybutyric acid-glycolic acid copolymer may be used in a mixture with polylactic acid. Although the polylactic acid may be of the D- or L-configuration or a mixture thereof, it is preferable that the ratio of the D-/L-configuration (moles) fall within the range from about 75/25 to about 20/80. The ratio of the D-/L-configuration (mole %) is more preferably about 60/40 to about 25/75, and still more preferably about 55/45 to about 25/75. The weight-average molecular weight of polylactic acid is preferably about 1,500 to about 20,000, more preferably about 1,500 to 10,000. Also, the degree of dispersion of the polylactic acid is preferably about 1.2 to 4.0, more preferably about 1.5 to 3.5.

For producing polylactic acid, two methods are known: ring-opening polymerization of lactide, a dimer of lactic acid, and dehydration polymerization condensation of lactic acid. For obtaining a polylactic acid of relatively low molecular weight for the present invention, direct dehydration polymerization condensation of lactic acid is preferred. This method is, for example, described in Japanese Patent Unexamined Publication No. 28521/1986.

When a 2-hydroxybutyric acid-glycolic acid copolymer and polylactic acid are used in mixture, their mixing ratio is about 10/90 to about 90/10 (% by weight). The mixing ratio is preferably about 20/80 to 80/20, and more preferably about 30/70 to 70/30.

In the present specification, weight-average molecular weight is defined as the molecular weight obtained by gel permeation chromatography (GPC) with 9 polystyrenes as reference substances with respective weight-average molecular weights of 120,000, 52,000, 22,000, 9,200, 5,050, 2,950, 1,050, 580 and 162. Number-average molecular weight based on GPC measurement is also calculated. The degree of dispersion is calculated from the weight-average molecular weight and the number-average molecular weight. Measurements were taken using a GPC column KF804L×2 (produced by Showa Denko) and an RI monitor L-3300 (produced by Hitachi, Ltd.) with chloroform as the mobile phase.

The above-described polymer and copolymer, synthesized by catalyst-free dehydration polymerization condensation, usually has a terminal carboxyl group.

In the present invention, the biodegradable polymer preferably has a terminal carboxyl group.

A biodegradable polymer having a terminal carboxyl group is a polymer in which the number-average molecular weight by GPC determination and that by terminal group determination almost agree.

By terminal group quantitation, number-average molecular weight is calculated as follows:

About 1 to 3 g of the biodegradable polymer is dissolved in a mixed solvent of acetone (25 ml) and methanol (5 ml), and the solution is quickly titrated with a 0.05N alcoholic solution of potassium hydroxide while being stirred at room temperature with phenolphthalein as an indicator to determine the terminal carboxyl group content; the number-average molecular weight based on terminal group quantitation is calculated using the following equation:

Number-average molecular weight based on terminal group quantitation=20,000 A/B

A: Weight mass (g) of the biodegradable polymer

B: Amount (ml) of the 0.05N alcoholic solution of potassium hydroxide added until the titration end point is reached.

For example, in the case of a polymer having a terminal carboxyl group, and synthesized from one or more α-hydroxy acids by catalyst-free dehydration polymerization condensation, the number-average molecular weight based on GPC measurement and the number-average molecular weight based on terminal group quantitation almost agree. On the other hand, in the case of a polymer having essentially no terminal carboxyl group, and synthesized from a cyclic dimer by ring-opening polymerization using a catalyst, the number-average molecular weight based on terminal group quantitation is significantly higher than the number-average molecular weight based on GPC determination. This difference makes it possible to clearly differentiate a polymer having a terminal carboxyl group from a polymer having no terminal carboxyl group.

While the number-average molecular weight based on terminal group quantitation is an absolute value, the number-average molecular weight based on GPC determination is a relative value that varies depending on various analytical conditions (e.g., kind of mobile phase, kind of column, reference substance, slice width chosen, baseline chosen etc.); it is therefore difficult to have an absolute numerical representation of the latter. However, the fact that the number-average molecular weight based on GPC determination and that based on terminal group quantitation almost agree means that the number-average molecular weight based on terminal group quantitation falls within the range from about 0.5 to about 2 times, preferably from about 0.8 to about 1.5 times, the number-average molecular weight based on GPC determination. Also, the fact that the number-average molecular weight based on terminal group quantitation is significantly higher than that based on GPC determination means that the number-average molecular weight based on terminal group quantitation is about 2 times or more the number-average molecular weight based on GPC determination.

The sustained-release preparation of the present invention is produced by dispersing in a biodegradable polymer a water-insoluble or a slightly water-soluble polyvalent metal salt of a physiologically active substance obtained by mixing the physiologically active substance and a water-soluble polyvalent metal salt. Methods of producing a sustained-release preparation include the in-water drying method, phase separation method, spray drying method, and modifications thereof.

Methods of producing a sustained-release preparation, e.g., microcapsules, are described below.

(i) In-water drying method (o/w method)

In this method, a solution of a biodegradable polymer in an organic solvent is first prepared. The organic solvent used to produce the sustained-release preparation of the present invention preferably has a boiling point not higher than 120° C. Such organic solvents include halogenated hydrocarbons (e.g., dichloromethane, chloroform, carbon tetrachloride etc.), alcohols (e.g., ethanol, methanol), acetonitrile and so on. These may be used in mixture at appropriate ratios. For example, when a dichloromethane and alcohols are used in mixture, their mixing ratio (v/v) is about 1000/1 to about 1/1, preferably about 100/1 to about 1/1, still more preferably about 10/1 to about 2/1. The organic solvent is preferably dichloromethane and acetonitrile, and still more preferably dichloromethane. The concentration of the biodegradable polymer in the organic solvent solution is normally about 0.01 to about 80% (w/w), preferably about 0.1 to about 70% (w/w), and more preferably about 1 to about 60% (w/w), depending on the molecular weight of the biodegradable polymer, kind of organic solvent and so on.

To the organic solvent solution of the biodegradable polymer thus obtained, a water-insoluble or a slightly water-soluble polyvalent metal salt of a physiologically active substance is added or dissolved, after being freeze-dried or vacuum dried as necessary. In this operation, the amount of complex added is set so that the complex:biodegradable polymer weight ratio is up to about 1:2, preferably about 1:3.

The organic solvent solution thus prepared is added to an aqueous phase to form an o/w emulsion using a turbine type mechanical stirrer or the like, followed by evaporation of the solvent in the oil phase, to yield microcapsules. The volume of the aqueous phase is normally chosen over the range of about 1 to about 10,000 times, preferably about 2 to about 5,000 times, and more preferably about 5 to about 2,000 times, the volume of the oil phase.

An emulsifier may be added to the external aqueous phase. The emulsifier may be any one, as long as it is capable of forming a stable o/w emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin, hyaluronic acid and so on. These may be used in combination as appropriate. The emulsifier concentration in the external aqueous phase is preferably about 0.001 to about 20% (w/w), more preferably about 0.01–about 10% (w/w), and still more preferably about 0.05–about 5% (w/w).

In the above-described o/w method, microcapsules may be produced by a method in which the complex is dispersed in an organic solvent solution of a biodegradable polymer, i.e., the s/o/w method.

(ii) In-water drying method (w/o/w method)

In this method, a solution of a biodegradable polymer in an organic solvent is first prepared. The concentration of the biodegradable polymer in the organic solvent solution is normally about 0.01 to about 80% (w/w), preferably about 0.1 to about 70% (w/w), and more preferably about 1 to about 60%, depending on the molecular weight of the biodegradable polymer, kind of organic solvent and so on. An aqueous dispersion of the complex is used as the internal aqueous phase. The concentration of the complex in the aqueous dispersion is, for example, about 10 to about 90% (w/v). The above-described aqueous dispersion of the complex is emulsified and dispersed in the organic solvent solution of the biodegradable polymer to form a w/o emulsion by known methods of dispersion using a turbine type mechanical stirrer, homogenizer and so on. This operation is conducted in such a way as to bring the weight ratio of the internal aqueous phase and the biodegradable polymer up to about 1:2, preferably about 1:3. The ratio of the internal aqueous phase and the organic solvent solution of the biodegradable polymer is 1:1,000 to 1:1 (v/v), preferably 1:100 to 1:5 (v/v), and more preferably 1:50 to 1:5 (v/v).

The w/o emulsion thus prepared is then added to another aqueous phase to form a w/o/w emulsion, followed by evaporation of the solvent in the oil phase, to yield microcapsules. This operation is conducted in accordance with term (i) above.

The sustained-release preparation of the present invention is preferably used in the form of fine particles. This is because sustained-release preparation does not cause undue pain to the patient when administered via an injection needle for ordinary subcutaneous or intramuscular injection. The mean particle diameter of the sustained-release preparation, for example, is about 0.1 to about 300 $\mu$m, preferably about 1 to about 150 $\mu$m, and more preferably about 2 to about 100 $\mu$m.

In the present specification, a sustained-release preparation in fine particle form is also referred to as a microcapsule.

As used herein the term "microcapsule" may be referred to as "microsphere".

The sustained-release preparation of the present invention can, for example, be administered as microcapsules as such, or in the form of various dosage forms of non-oral preparations (e.g., intramuscular, subcutaneous or visceral injections or indwellable preparations, nasal, rectal or uterine transmucosal preparations etc.) or oral preparations (e.g., capsules such as hard capsules, soft capsules etc., solid preparations such as granules and powders etc., liquid preparations such as suspensions etc.).

In the present invention, the sustained-release preparation is preferably used for injection. When the sustained-release preparation is a microcapsule, for instance, it can be prepared as an aqueous suspension by suspending microcapsules in water, along with a dispersing agent (e.g., surfactants such as Tween 80 and HCO-60, polysaccharides such as carboxymethyl cellulose, sodium alginate and sodium hyaluronate etc.), a preservative (e.g., methyl paraben, propyl paraben etc.), an isotonizing agent (e.g., sodium chloride, mannitol, sorbitol, glucose etc.), etc., to yield a sustained-release preparation for injection of practical use.

Alternatively, the sustained-release preparation of the present invention is prepared as an oily suspension by dispersing microcapsules, along with a vegetable oil such as sesame oil or corn oil with or without a phospholipid such as lecithin, or a medium-chain fatty acid triglyceride (e.g., MIGLYOL 812), to yield a sustained-release preparation for injection of practical use.

When the sustained-release preparation is a microcapsule, for instance, its mean particle size is chosen over the range from about 0.1 to about 300 μm as long as the requirements concerning degree of dispersion and needle passage are met, when it is to be used as an injectable suspension. Preferably, the particle size falls within the range from about 1 to about 150 μm, more preferably about 2 to about 100 μm.

The above-described microcapsule can be prepared as a sterile preparation, without limitation by the method in which the entire production process is sterile, the method in which gamma rays is used as sterilant, and the method in which an antiseptic is added.

With low toxicity, the sustained-release preparation of the present invention can be safely used in mammals (e.g., humans, bovines, swines, dogs, cats, mice, rats, rabbits etc.).

Indications for the sustained-release preparation of the present invention vary according to the physiologically active substance used. For example, the sustained-release preparation of the present invention is effective in the treatment or prevention of diabetes mellitus etc. when the physiologically active substance is insulin; renal cancer, hepatitis C etc. when the physiologically active substance is interferon alpha; anemia etc. when the physiologically active substance is erythropoietin; developmental failure when the physiologically active substance is growth hormone, and neutropenia etc. after anticancer chemotherapy when the physiologically active substance is granulocyte colony-stimulating factor. When the physiologically active substance is erythropoietin, the sustained-release preparation of the present invention is also effective in promoting hematopoiesis for autotransfusion.

Depending on the type and content of the physiologically active substance, duration of physiologically active substance release, target disease, subject animal and other factors, the dose of the sustained-release preparation may be set at levels such that the physiologically active substance exhibits its action. The dose per administration of the physiologically active substance is chosen as appropriate over the range from about 0.0001 to about 10 mg/kg body weight for each adult, when the preparation is a 1-week preparation. More preferably, the dose may be chosen as appropriate over the range about about 0.0005 to about 1 mg/kg body weight.

The dose per administration of the sustained-release preparation is preferably chosen as appropriate over the range from about 0.0005 to about 50 mg/kg body weight for each adult. More preferably, the dose is chosen as appropriate over the range from about 0.0025 to about 10 mg/kg body weight. Dosing frequency can be chosen as appropriate, e.g., once weekly, once every two weeks or once every four weeks, depending on type, content and dosage form of the physiologically active substance, duration of physiologically active substance release, subject disease, subject animal and other factors.

Although the preparation of the present invention may be stored at normal temperature or in a cold place, it is preferable to store it in a cold place. Normal temperature and a cold place as mentioned herein are as defined by the Pharmacopoeia of Japan, specifically, 15 to 25° C. for normal temperatures and under 15° C. for cold places.

BEST MODE FOR CARRYING OUT THE INVENTION

The present invention is hereinafter described in more detail by means of the following examples, which are not to be construed as limitative.

REFERENCE EXAMPLE 1

A solution of 0.5 g of swine insulin (27.3 U/mg, DIOSYNTH, Netherlands) in 22 ml of 100 mM sodium hydroxide aqueous solution and a solution of 1 g of zinc acetate (dihydrate) in 10 ml of distilled water were mixed together and kept standing at room temperature for 1 hour. After centrifugation at about 3,000 rpm (O5PR-22, Hitachi, Ltd.), the supernatant was discarded. The residue was again dispersed in distilled water and centrifuged. After the supernatant was discarded, a small amount of distilled water was added to the residue, which was then freeze-dried to yield about 1 g of crude zinc salt of swine insulin as a dry powder.

To determine the insulin content in the powder thus obtained, the powder was extracted with a 50 mM EDTA solution containing 30% acetonitrile being shaken for 3 hours, followed by quantitation by high performance liquid chromatography (HPLC). It was shown that 47.6 mg of swine insulin was contained per 100 mg of dry powder.

REFERENCE EXAMPLE 2

To a mixture of 168 ml of 40% aqueous solution of potassium hydroxide and 1,000 ml of ethyl ether, 104 g of nitrosoethylurea was added little by little, while the mixture was stirred under ice cooling conditions. The resulting yellow ether layer was separated and dried by the addition of granular potassium hydroxide. The potassium hydroxide was then removed to yield about 900 ml of a diazoethane solution.

130 g of a lactic acid-glycolic acid copolymer (lactic acid/glycolic acid=50/50 (mole %) of about 5,800 in weight-average molecular weight) was dissolved in 1,900 ml of methylene chloride, stirred and cooled. Under ice cooling conditions, the above diazoethane solution was added drop by drop, followed by stirring at room temperature for 2 hours. After the mixture was kept standing overnight, the solvent was distilled off under reduced pressure; the residue was vacuum dried at room temperature to yield 131 g of the ethyl ester of the lactic acid-glycolic acid copolymer.

REFERENCE EXAMPLE 3

A solution of 1 mg of human growth hormone (Biotechnology General, USA) in 0.9 ml of distilled water and a solution of 9.98, 29.43, 49.88, 69.84, 79.81 or 99.77 μg of zinc acetate (dihydrate) in 0.1 ml of distilled water were mixed together. A molar ratio of zinc atom to growth hormone are 1, 3, 5, 7, 8 and 10. In case of the molar ratio being 5, about 60% of the human growth hormone was precipitated. In case of the molar ratio being 7 or more, almost 100% of the human growth hormone was precipitated.

REFERENCE EXAMPLE 4

1 g of leuprolide acetate (TAP-144) and 157.5 mg of gelatin were dissolved in 1 ml of distilled water at 70 to 80° C. To the aqueous solution warming at the temperature being slightly higher than the gelation temperature of the aqueous solution, 21 g of solution of lactic acid-glycolic acid copolymer, which was prepared by dissolving 7.85 g of the lactic acid-glycolic acid copolymer [lactic aicd/glycolic acid: 75/25 (mole %), viscosity: 0.142 to 0.169 cP] in 13.15 g of dichloromethane, was added. The mixture was emulsified with a compact homogenizer for several minutes or more to provide a W/O emulsion. The obtained W/O emulsion was cooled to 10 to 20° C. The emulsion was poured in 5000 ml of 0.1% (w/v) aqueous polyvinyl alcohol solution which temperature was adjusted to 10 to 20° C. and the mixture was emulsified using a turbine homomixer to provide a W/O/W emulsion. This W/O/W emulsion was stirred at room temperature (15 to 30° C.) to evaporate the dichloromethane and, thereby, solidify the internal W/O emulsion, after which the microcapsules were collected by centrifugation. These microcapsules were redispersed in distilled water and further centrifuged to wash off the excess drug and polyvinyl alcohol. The recovered microcapsules were suspended in a small amount of distilled water. To the suspension, 1.5 g of D-mannitol was added and dissolved. The obtained suspension was freeze-dried under reduced pressure to provide powdery microcapsules.

After lyophilization, the obtained microcapsules as a powder were further dried at 50° C. under reduced pressure, viz. a temperature 3° C. higher than Tmg of the matrix component lactic acid-glycolic acid copolymer, for 24, 48, 96 or 120 hours to provide powdery sustained-release microcapsules.

EXAMPLE 1

To 200 ml of an aqueous solution of interferon alpha (containing 40 billion IU), 1 ml of an aqueous solution of zinc acetate (dihydrate) (200 mg/ml) and 1 ml of 1N sodium hydroxide were added; after mixing, the mixture was kept standing at 4° C. overnight. After centrifugation at 3,000 rpm, the insoluble complex was recovered and freeze-dried to yield about 200 mg of crude zinc salt of interferon alpha.

To a solution of 1.5 g of a lactic acid-glycolic acid copolymer (lactic acid/glycolic acid ratio=50/50, molecular weight 5,800, produced by Wako Pure Chemical Industries) and 1.5 g of the ethyl ester of lactic acid-glycolic acid copolymer obtained in Reference Example 2 in 4 ml of dichloromethane, 200 mg of the above-described crude zinc salt of interferon alpha was added, followed by stirring for about 30 seconds using a homogenizer (Polytron) to yield an s/o emulsion. This emulsion was poured in 700 ml of a 0.1% (w/w) aqueous solution of polyvinyl alcohol (EG-40, produced by The Nippon Synthetic Chemical Industry) previously adjusted to 18° C., followed by stirring in a turbine homomixer at 6,000 rpm to yield an s/o/w emulsion. This emulsion was stirred at room temperature for 3 hours to volatilize the dichloromethane and solidify the oil phase. Subsequently, after centrifugation at about 2,000 rpm (05PR-22, Hitachi, Ltd.), the supernatant was discarded. The resulting residue was again dispersed in distilled water and centrifuged. After the collected microcapsules were re-dispersed in a small amount of distilled water in the presence of 50 mg of D-mannitol, the dispersion was freeze-dried to yield powder microcapsules.

EXAMPLE 2

3.6 g of a lactic acid-glycolic acid copolymer (lactic acid/glycolic acid=75/25 (mole %), weight-average molecular weight 13,585, number-average molecular weight 4,413, produced by Wako Pure Chemical Industries) was dissolved in 6.6 g (5 ml) of dichloromethane. 420 mg of the crude zinc salt of swine insulin obtained in Reference Example 1 (containing 200 mg of swine insulin) was dispersed in 6.6 g (5 ml) of dichloromethane. Both were mixed and stirred for about 10 seconds in a homogenizer (Polytron) to yield an s/o emulsion. This emulsion was poured in 800 ml of a 0.1% (w/w) aqueous solution of polyvinyl alcohol (EG-40, produced by The Nippon Synthetic Chemical Industry), previously adjusted to 18° C., followed by stirring in a turbine homomixer at 6,000 rpm to yield an s/o/w emulsion. This emulsion was then stirred at room temperature for 3 hours to volatilize the dichloromethane and solidify the oil phase. After centrifugation at about 2,000 rpm (05PR-22, Hitachi, Ltd.), the supernatant was discarded. The residue was again dispersed in distilled water and centrifuged. After the collected microcapsules were re-dispersed in a small amount of distilled water in the presence of 50 mg of D-mannitol, the dispersion was freeze-dried to yield powder microcapsules (about 3 g recovered).

To determine the insulin content in the microcapsules thus obtained, the powder was extracted by shaking with a 50 mM EDTA solution containing 30% acetonitrile for 3 hours, followed by quantitation by high performance liquid chromatography (HPLC). It was shown that 6.2 mg of insulin was contained per 100 mg of microcapsules.

EXAMPLE 3

To 8 ml of an erythropoietin injection solution (Espo™ Injection 3000, produced by Sankyo) (containing 12,000 IU), 1 g of zinc chloride was added little by little; the mixture was kept standing at room temperature for 1 hour. After the mixture was centrifuged at 3,000 rpm, the precipitate was again dispersed in distilled water and centrifuged to yield a precipitate. To this precipitate, a small amount of distilled water was added, followed by freeze-drying, to yield 60 mg of a mixture of crude zinc salt of erythropoietin and crude zinc salt of albumin as a powder.

To a solution of 0.5 g of a lactic acid-glycolic acid copolymer (lactic acid/glycolic acid ratio=50/50, molecular weight 14,000, produced by Wako Pure Chemical Industries) in 1.5 ml of dichloromethane, 60 mg of the above-described mixture of crude zinc salt of erythropoietin and crude zinc salt of albumin was added, followed by stirring for about 30 seconds using a homogenizer (Polytron), to yield an s/o emulsion. This emulsion was then treated in the same manner as in Example 1 to yield 152 mg of powder microcapsules.

EXAMPLE 4

Human growth hormone (Genotropin™ 16IU, produced by Sumitomo Pharmaceuticals) was dissolved in 1 ml of distilled water. To this solution, 100 μl of an aqueous solution of zinc chloride (10 mg/ml) was added; the mixture was kept standing at room temperature for 1 hour. The mixture was then centrifuged; the precipitate was again dispersed in distilled water and centrifuged to yield a precipitate. To this precipitate, a small amount of distilled water was added, followed by freeze-drying, to yield 5.6 mg of crude zinc salt of human growth hormone as a powder.

To a solution of 0.5 g of a lactic acid-glycolic acid copolymer (lactic acid/glycolic acid ratio=75/25, molecular weight 9,800, produced by Wako Pure Chemical Industries) in 1.5 ml of dichloromethane, 5.6 mg of the above-described crude zinc salt of human growth hormone was added, followed by stirring for about 30 seconds using a homogenizer (Polytron), to yield an s/o emulsion. This emulsion was then treated in the same manner as in Example 1 to yield 121 mg of powder microcapsules.

EXAMPLE 5

After 10 ml (containing 3×10$^8$ IU) of a granulocyte colony-stimulating factor (G-CSF) injection solution

[Filgrastin Neupogen, trade name, Amgen, USA) was neutralized with a dilute aqueous solution of sodium hydroxide, 1 ml of an aqueous solution of zinc chloride (10 mg/ml) was added; the mixture was kept standing at room temperature for 1 hour. The mixture was then centrifuged; the precipitate was again dispersed in distilled water and centrifuged to yield a precipitate. To this precipitate, a small amount of distilled water was added, followed by freeze-drying, to yield 4 mg of crude zinc salt of granulocyte colony-stimulating factor as a powder.

To a solution of 0.5 g of a lactic acid-glycolic acid copolymer (lactic acid/glycolic acid ratio=50/50, molecular weight 8,000, produced by Wako Pure Chemical Industries) in 1.5 ml of dichloromethane, 4 mg of the above-described crude zinc salt of granulocyte colony stimulating factor was added, followed by stirring for about 30 seconds using a homogenizer (Polytron), to yield an s/o emulsion. This emulsion was then treated in the same manner as in Example 1 to yield 110 mg of powder microcapsules.

EXAMPLE 6

After 5.21 mg (26 U/mg) of human insulin (human recombinant insulin, purchased from Wako Pure Chemical Industries) was dissolved in 0.63 ml of a 57 mM aqueous solution of hydrochloric acid, 0.35 ml of a 0.05N aqueous solution of sodium hydroxide was added to yield a human insulin solution of nearly neutral pH. To this human insulin solution, 0.2 ml of an aqueous solution of zinc acetate (20 mg/ml) was added; the mixture was kept standing at 4° C. overnight. The mixture was then centrifuged at about 3,000 rpm; the precipitate was again dispersed in distilled water and centrifuged to yield a precipitate. To this precipitate, a small amount of distilled water was added, followed by freeze-drying, to yield 11 mg of crude zinc salt of human insulin as a powder.

To a solution of 0.5 g of a lactic acid-glycolic acid copolymer (lactic acid/glycolic acid ratio=50/50, molecular weight 6,000, produced by Wako Pure Chemical Industries) in 1.5 ml of dichloromethane, 11 mg of the above-described crude zinc salt of human insulin was added, followed by stirring for about 30 seconds using a homogenizer (Polytron), to yield an s/o emulsion. This emulsion was then treated in the same manner as in Example 1 to yield 105 mg of powder microcapsules.

COMPARATIVE EXAMPLE

To a solution of 0.9 g of lactic acid-glycolic acid copolymer [lactic acid/glycolic acid ratio=50/50 (mole %), weight-average molecular weight 6,000, produced by Wako Pure Chemical Industries] in 1.5 ml of dichloromethane, 100 mg of a substantially zinc free human insulin [zinc content being under 0.0001% (w/w)] was added, followed by stirring for about 10 seconds using a homogenizer (Polytron), to yield an s/o emulsion. This emulsion was then treated in the same manner as in Example 1 to yield powder microcapsules (470 mg).

To determine the insulin content in the microcapsules thus obtained, the powder was extracted by shaking with a 50 mM EDTA solution containing acetonitrile for 3 hours, followed by quantitation by high performance liquid chromatography (HPLC). It was shown that 8.7 mg of insulin was contained per 100 mg of microcapsules.

EXPERIMENTAL EXAMPLE 1

323 mg of powder microcapsules as obtained in Example 2 was dispersed in a 1 ml of dispersant for injection (5 mg of carboxymethyl cellulose, 1 mg of polysorbate 80 and 50 mg of mannitol dissolved per ml distilled water). The resulting dispersion was subcutaneously administered to the backs of 6-week-old male SD rats (insulin administered at about 20 mg per rat). After administration, blood was collected via the tail at constant intervals and assayed for serum swine insulin concentration using an enzyme immunoassay (EIA) kit (produced by Sanko Junyaku). Active swine insulin was detected in serum for 1 week or more after administration.

EXPERIMENTAL EXAMPLE 2

70 mg of powder microcapsules as obtained in Example 4 was dispersed in a 0.5 ml of dispersant for injection (5 g of carboxymethyl cellulose, 2 g of polysorbate 80 and 50 g of mannitol dissolved per liter distilled water). The resulting dispersion was subcutaneously administered to the backs of 6-week-old male SD rats (growth hormone administered at about 3 mg per rat). After administration, blood was collected via the tail at constant intervals and assayed for serum growth hormone concentration by radio immunoassay. Active growth hormone was detected in serum for 1 week or more after administration.

COMPARATIVE EXPERIMENTAL EXAMPLE 154.7 mg of powder microcapsule as obtained in Comparative Example was dispersed in a 1.75 ml of dispersant for injection (5 mg of carboxymethyl cellulose, 1 mg of polysorbate 80 and 50 mg of mannitol dissolved per ml distilled water). The resulting dispersion was subcutaneously administered to the backs of 6-week-old male SD rats (insulin administered at about 44 mg per rat). After administration, blood was collected via the tail at constant intervals and assayed for serum insulin concentration by an enzyme immunoassay (EIA). Active insulin was detected in serum only at 1 day after administration.

INDUSTRIAL APPLICABILITY

According to the present invention, it is possible to provide a sustained-release preparation that is highly efficient in incorporating physiologically active substance and suppresses initial physiologically active substance burst. The sustained-release preparation of the present invention is capable of releasing the physiologically active substance while retaining its bioactivity after administration in vivo. Furthermore, the physiologically active substance in the sustained-release preparation is kept stable for a long period of time, with little loss of bioactivity.

The following disclosure on pages 32–86 relates to a second embodiment of a sustained-release preparation which comprises an anti-endothelin substance.

FIELD OF THE SECOND EMBODIMENT

The second embodiment of the present invention relates to a sustained-release preparation of an anti-endothelin substance, such as an endothelin antagonist, used to treat endothelin associated diseases, particularly chronic diseases, such as chronic complications in diabetes mellitus.

BACKGROUND OF THE SECOND EMBODIMENT

Showing various potent physiological actions, peptides have been applied as pharmaceuticals in numerous attempts. Their biological half-life, however, is usually very short. Therefore, for a sustained pharmacologic effect, peptides must be frequently administered, resulting in severe suffering by the patient. Endothelin, a peptide secreted by the vascular endothelium, shows vascular smooth muscle constricting action, both potent and sustainable. Endothelin is therefore important both physiologically and pathologically. Also, there have been reports of the development of peptide-based endothelin antagonists, with the strong expectation that anti-endothelin substances such as endothelin receptor antagonists will contribute to the treatment of various diseases associated with endothelin. For the reasons described above, however, the application of such peptide-based antagonists as pharmaceuticals has been limited. Also, in therapeutic application of conventional endothelin antagonists, there have been attempts to prevent the onset and progress of pathologic states by antagonizing endothelin-associated reactions in acute diseases such as attacks and shocks of acute myocardial infarction. Although application to the treatment of hypertension, cardiac/cerebral circulatory diseases, renal diseases and other diseases has been suggested, there is no specific exemplification. Nor has there been any finding that administration of endothelin antagonists is effective in preventing the onset and progress of endothelin-associated pathologic states in chronic diseases such as diabetic nephropathy.

Various sustained-release preparations are known, including the release rate controlling system based on a polymeric matrix containing a polypeptide dispersed in a poly(lactide-glycolide) copolymer, described in Japanese Patent Unexamined Publication No. 2930/1988 (EP-A-25 1476).

Japanese Patent Examined Publication No. 40329/1992 (Japanese Patent Unexamined Publication No. 118512/1982, EP-A-52510) discloses a composition comprising a biodegradable poly(lactide-glycolide) copolymer which is biologically compatible with luteinizing hormone-releasing hormone (LH-RH) or an analog thereof, a water-soluble polypeptide, and which is capable of sustained release of an effective amount of the polypeptide over a period of at least 1 month.

Japanese Patent Unexamined Publication No. 124814/1990 (EP-A-350246) discloses an art in which a water-soluble drug is effectively packed in microcapsules by adding drug retaining substance comprising an organic basic substance such as a basic amino acid and using a wall made of polymer, and excessive drug release just after administration is suppressed.

There is no sustained-release preparation which comprises a combination of an anti-endothelin substance and a biodegradable polymer and which is capable of effective sustained release of the anti-endothelin substance at an almost constant rate.

Against the above background there is a need for an excellent sustained-release preparation for the treatment of chronic diseases caused by endothelin.

SUMMARY OF THE SECOND EMBODIMENT

According to the present invention, there is provided:
(1) a sustained-release preparation which comprises an anti-endothelin substance and a biodegradable polymer,
(2) the sustained-release preparation according to (1) above, wherein the anti-endothelin substance is an endothelin antagonist,
(3) the sustained-release preparation according to (2) above, wherein the endothelin antagonist is a peptide,
(4) the sustained-release preparation according to (2) above, wherein the endothelin antagonist is a peptide of the general formula:

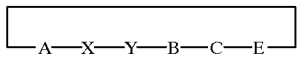

wherein X and Y independently represent an α-amino acid residue; A represents a D-acidic-α-amino acid residue; B represents a neutral-α-amino acid residue; C represents an L-α-amino acid residue; E represents a D-α-amino acid residue having an aromatic cyclic group, or an ester thereof, or a salt thereof,
(5) the sustained-release preparation according to (4) above, wherein the peptide is a compound of the formula cyclo [—D—Asp—Asp(R1')-Asp-D-Thg(2)—Leu—D—Trp—] wherein Asp represents aspartic acid; Asp(R1') represents aspartic acid β-4-phenylpiperazinamide; and Thg(2) represents 2-thienylglycine; Leu represents leucine; Trp represents tryptophan,
(6) the sustained-release preparation according to (4) above, wherein A is a D-acidic-α-amino acid residue which is esterified with an alkyl group,
(7) the sustained-release preparation according to (4) above, wherein Y is a L-acidic-α-amino acid residue,
(8) the sustained-release preparation according to (4) above, wherein Y is a L-acidic-α-amino acid residue which is esterified with an alkyl group,
(9) the sustained-release preparation according to (4) above, wherein the peptide is a compound of the formula, cyclo-[—D—Asp($OC_2H_5$)—Asp(R1')—Asp($OC_2H_5$)—D—Thg(2)—Leu—D—Trp—], wherein Asp represents aspartic acid; Asp(R1') represents aspartic acid β-4-phenylpiperazinamide; Thg(2) represents 2-thienylglycine; Leu represents leucine; and Trp represents tryptophan,
(10) the sustained-release preparation according to (4) above, wherein the salt is a polyvalent metal salt,
(11) the sustained-release preparation according to (10) above, wherein the polyvalent metal salt is a zinc salt,
(12) the sustained-release preparation according to (1) above, wherein the biodegradable polymer is an aliphatic polyester,
(13) the sustained-release preparation according to (12) above, wherein the aliphatic polyester is a copolymer of glycolic acid and lactic acid,
(14) the sustained-release preparation according to (13) above, wherein the copolymer has a weight-average molecular weight of about 2,000 to 50,000, as determined by Gel Permeation Chromatography,
(15) the sustained-release preparation according to (13) above, wherein the copolymer has a dispersity of about 0.2 to 4.0,
(16) the sustained-release preparation according to (1) above, which further comprises an organic basic substance,
(17) the sustained-release preparation according to (1) above, which further comprises a water-soluble polyvalent metal salt,
(18) a method for treatment of diseases caused by endothelin comprising administering to a patient in need thereof an effective amount of the sustained-release preparation according to (1) above,
(19) the method according to (18) above, wherein the diseases are chronic diseases,
(20) the method according to (19) above, wherein the chronic diseases are chronic complications in diabetes mellitus,
(21) the method according to (20) above, wherein the chronic complications are diabetic nephropathy,

(22) an injectable preparation which comprises the sustained-release preparation according to (1) above.

(23) a peptide of the general formula:

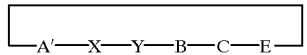

[II]

wherein X and Y independently represent an α-amino acid residue; A' represents a D-acidic-α-amino acid residue which is esterified with an alkyl group; B represents a neutral-α-amino acid residue; C represents an L-α-amino acid residue; E represents a D-α-amino acid residue having an aromatic cyclic group, or a salt thereof,

(24) the peptide according to (23) above, wherein X is an L-isomer,

(25) the peptide according to (23) above, wherein Y is an L-isomer,

(26) the peptide according to (23) above, wherein A' is D-glutamic acid or D-aspartic acid which is esterified with an alkyl group,

(27) the peptide according to (23) above, wherein B is an D-isomer,

(28) the peptide according to (23) above, wherein B is selected from the group consisting of D-leucine, D-alloisoleucine, D-tertiary leucine, D-gamma methyl leucine, D-phenylglycine, D-2-thienylglycine, D-3-thienylglycine, D-2-cyclopentylglycine, D-phenylalanine, D-2-thienylalanine, D-valine, D-2-furylglycine and D-3-furylglycine residues,

(29) the peptide according to (23) above, wherein C is selected from the group consisting of L-leucine, L-phenylalanine and L-tryptophan residues,

(30) the peptide according to (23) above, wherein E is selected from the group consisting of D-tryptophan or derivatives thereof, D-1-naphthylalanine, D-2-naphthylalanine, D-benzothienylalanine, D-4-bisphenylalanine and D-pentamethyl phenylalanine residues,

(31) the peptide according to (23) above, wherein Y is an α-amino acid residue having a carboxyl group which is esterified with an alkyl group,

(32) a peptide according to the formula: cyclo-[—D—Asp($OC_2H_5$)—Asp(R1')—Asp($OC_2H_5$)—D—Thg(2)—Leu—D—Trp—], wherein Asp represents aspartic acid; Asp(R1') represents aspartic acid β-4-phenylpiperazinamide; Thg(2) represents 2-thienylglycine; Leu represents leucine; and Trp represents tryptophan, or a salt thereof, and

(33) a zinc salt of a peptide represented by the general formula:

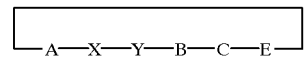

[I]

wherein X and Y independently represent an α-amino acid residue; A represents a D-acidic-α-amino acid residue; B represents a neutral-α-amino acid residue; C represents an L-α-amino acid residue; E represents a D-α-amino acid residue having an aromatic cyclic group.

As the pathologic state of diabetics is better managed as a result of advances in medicine and pharmacology, the life span of diabetics is increasing also. The extended period of the diabetic condition, however, has raised the problem of chronic complications, especially vascular disorders. Vascular disorders are known to cause various organ disorders because the former occur in coronary arteries, cerebral arteries and microvessels such as those in the retina and renal glomeruli. An example of a chronic complication in diabetes mellitus is nephropathy. Although many factors have been suggested as being involved in the onset of diabetic nephropathy, mesangial thickening and mesangial cell proliferation are marked pathologic factors. It has been assumed that such mesangial thickening eventually destroys glomeruli, causing terminal renal failure. Endothelin, secreted from vascular endothelial cells, is known to be released in large amounts from damaged vessels. Based on the fact that in mesangial cells endothelin stimulates various reactions associated with cell proliferation, such as thymidine uptake, $Na^+/H^+$ exchange and c-fos expression, the possibility is suggested that chronic exposure to excess endothelin can be the initial stimulation to cause mesangial cell proliferation, suggesting the involvement of endothelin in diabetic nephropathy. In complications other than nephropathy (e.g., diabetic cardiomyopathy and diabetic retinopathy) as well, endothelin resulting from vascular disorders may be involved in the chronic fixation of the pathologic state. Also, since arteriosclerosis and hyperlipidemia are often seen in diabetes mellitus, with some disorder of endothelial cells, involvement of endothelin in these pathologic states is suspected. There are other endothelin-associated diseases, particularly chronic ones, whose onset and progress can be prevented by applying the therapy of the present invention for sustained retention of an anti-endothelin substance in the living body.

DETAILED DESCRIPTION OF THE SECOND EMBODIMENT

Where amino acids are expressed by abbreviations, the abbreviations recommended by IUPAC-IUB Commission on Biochemical Nomenclature (European Journal of Biochemistry 138, 9–37, 1984) or the abbreviations in common usage in the art are used. Where optical isomers exist for any compound, the L-isomer is meant unless otherwise indicated.

In the present invention, the anti-endothelin substance is exemplified by antibodies against endothelin, antibodies against endothelin receptors, high molecular substances represented by soluble endothelin receptors, endothelin antagonists obtained by chemical synthesis or fermentation, and substances which inhibit endothelin production (endothelin converting enzyme inhibitors).

The anti-endothelin substance in the present invention inhibits the binding of endothelin to its receptors. For example, the anti-endothelin substance inhibits the binding of endothelin-1 to a membrane fraction prepared from a homogenate of swine aortic smooth muscle. It is reported that there are at least two subtypes of endothelin receptors, referred to as ET-A and ET-B, respectively. The anti-endothelin substance in the present invention antagonizes one or both of these two receptors.

The anti-endothelin substance in the present invention inhibits vascular or muscular contraction induced by endothelin-1 administration in spiral specimens of swine coronary artery with the endothelial cells removed, specimens of the excised guinea pig tracheal muscle or specimens of the excised swine cerebral basal artery, antagonizes the increase in perfusion pressure by endothelin in excised rat hearts, and improves mortality in mice receiving endotoxin.

The anti-endothelin substance in the present invention may be water soluble or oil soluble. The degree of water solubility in the present invention is preferably octanol/water ratios of not higher than 0.1. The degree of oil solubility in the present invention is preferably octanol/water ratios of over 0.1. Also, the anti-endothelin substance may be soluble in polar solvents such as acetonitrile, dichloromethane and chloroform at not less than 10 mg/ml and not more than 100 mg/ml. It may also be almost insoluble in acetonitrile, dichloromethane and chloroform.

In the present invention, the anti-endothelin substance is preferably an endothelin antagonist, as exemplified by non-peptide compounds, peptides and derivatives thereof obtained by chemical synthesis or fermentation, peptides and derivatives thereof. Here, the peptide may be a chain or cyclic peptide or a cyclic and chain peptide.

Examples of non-peptide compounds include the non-peptides described in European Patent Publication Nos. 510526 and 526708 and WO93/08799.

(1) EPA-510526:
a compound represented by the formula

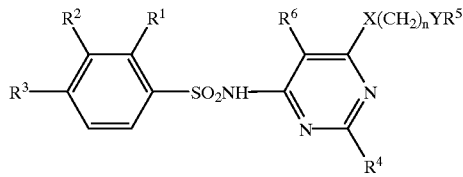

wherein
$R^1$: a hydrogen atom, lower-alkyl group, lower-alkoxy group, lower-alkylthio group, a halogen atom or trifluoromethyl;

$R^2$: a hydrogen atom, a halogen atom, lower-alkoxy group, hydroxy-lower-alkoxy group, or trifluoromethyl;

$R^3$: a hydrogen atom, hydroxy group, a halogen atom, alkylthio group, cycloalkyl group, hydroxy-lower-alkyl group, hydroxy-lower-alkoxy group, hydroximino-lower-alkyl lower-alkenyl group, oxo-lower-alkyl group, trifluoromethyl, trifluoromethoxy, lower-alkoxy group, lower-alkoxy-lower-alkoxy group, aryl-lower-alkoxy group;

$R^2$ and $R^3$: together to form butadienyl;

$R^4$: a hydrogen atom, lower-alkyl group, aryl group or heteroaryl group;

$R^5$: a hydrogen atom, lower-alkanoyl group, benzoyl, hetrocyclyl-carbonyl group, or tetrahydropyran-2-yl;

$R^6$ is represented by the formula (a) or (b)

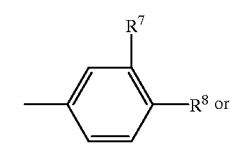

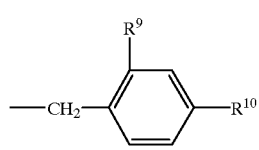

$R^7$: a hydrogen atom, lower-alkoxy group or nitro, and $R^8$ represents a hydrogen atom, a halogen atom, lower-alkyl group, lower-alkoxy group, lower-alkylthio group, nitro, hydroxy, amino or trifluoromethyl;

$R^7$ and $R^8$: together to form butadienyl;

$R^9$: a hydrogen atom, a halogen atom, lower-alkyl group, lower-alkoxy group, lower-alkylthio group or trifluoromethyl;

$R^{10}$: a hydrogen atom, a halogen atom, lower-alkyl group, lower-alkoxy group or lower-alkylthio group;

X and Y: independently O, S or NH;

n: 2, 3 or 4; or a salt thereof;

(2) EPA-526708:
a compound represented by the formula

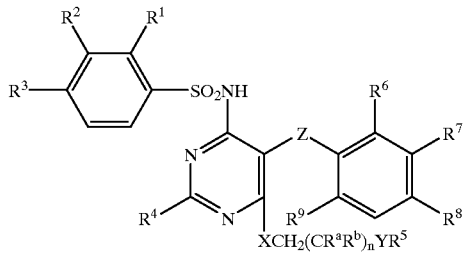

wherein
$R^1$: a hydrogen atom, lower-alkoxy group, lower-alkylthio group, a halogen atom or trifluoromethyl;

$R^2$: a hydrogen atom, a halogen atom, lower-alkoxy group, trifluoromethyl or —OCH$_2$COOR$^a$;

$R^3$: a hydrogen atom, a halogen atom, lower-alkyl group, lower-alkylthio group, cycloalkyl group, lower-alkoxy group or trifluoromethyl $R^2$ and $R^3$: together to form butadienyl, methylenedioxy, ethylenedioxy or isopropylidendioxy;

$R^4$: a hydrogen atom, lower-alkyl group, cycloalkyl group, trifluoromethyl, lower-alkoxy group, lower-alkylthio group, lower-alkylthio-lower-alkyl group, hydroxy-lower-alkyl group, hydroxy-lower-alkoxy group, lower-alkoxy-lower-alkyl group, hydroxy-lower-alkoxy-lower-alkyl group, hydroxy-lower-alkoxy-lower-alkoxy group, lower-alkylsulfinyl group, lower-alkylsulfonyl group, 2-methoxy-3-hydroxypropoxy, 2-hydroxy-3-phenylpropyl, amino-lower-alkyl group, lower-alkylamino-lower-alkyl group, di-lower-alkylamino-lower-alkyl group, amino, lower-alkylamino group, di-lower-alkylamino group, arylamino group, aryl group, arylthio group, aryloxy group, aryl-lower-alkyl group or heterocyclyl group;

$R^5$: a hydrogen atom, lower-alkyl group, lower-alkanoyl group, benzoyl, hetrocyclyl-carbonyl group, hetrocyclyl-methyl, or tetrahydropyran-2-yl;

$R^6$~$R^9$: a hydrogen atom, a halogen atom, trifluoromethyl, lower-alkyl group, lower-alkoxy group, lower-alkylthio group, hydroxy, hydroxymethyl, cyano, carboxyl, formyl, methyl sulfinyl, methyl sulfonyl, methyl sulfonyloxy, lower-alkoxy carbonyloxy;

$R^7$: together with $R^6$ or $R^8$ to form butadienyl, methylenedioxy, ethylenedioxy or isopropyliedenedioxy;

Z: —O—, —S—, ethylene, vinylene, —CO—, —OCHR$^{10}$— or —SCHR$^{10}$—;

$R^{10}$: a hydrogen atom or lower-alkyl group;

X and Y: independently O, S or NH;

YR$^5$: lower-alkyl sulfinyl or —OCH$_2$CH(OR$^c$)CH$_2$R$^d$;

$R^a$, $R^b$, $R^c$ and $R^d$: a hydrogen atom or lower-alkyl group;

$R^c$ and $R^d$: together to form methylene, ethylene or isopropylidene;

n: 1, 2 or 3; or a salt thereof;

(3) WO93/08799:
a compound of formula

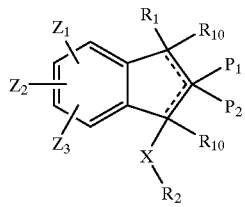

wherein:
$R_1$ is —X(CH$_2$)$_n$Ar or —X(CH$_2$)$_n$R$_8$ or

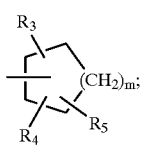

(c)

$R^2$ is hydrogen, Ar or (c);
$P_1$ is —X(CH$_2$)$_n$R$_8$;
$P_2$ is —X(CH$_2$)$_n$R$_8$, or —XR$_9$Y;
$R_3$ and $R_5$ are independently hydrogen, $R_{11}$, OH, $C_{1-8}$ alkoxy, S(O)$_q$R$_{11}$, N(R$_6$)$_2$, Br, F, I, Cl, CF$_3$, NHCOR$_6$, —XR$_9$—Y or —X(CH$_2$)$_n$R$_8$ wherein the methylene groups of —X(CH$_2$)$_b$R$_8$ may be substituted by one or more —(CH$_2$)$_n$Ar groups;
$R_4$ is hydrogen, $R_{11}$, OH, $C_{1-5}$ alkoxy, S(O)$_q$R$_{11}$, N(R$_6$)$_2$, —X(R$_{11}$), Br, F, I, Cl or NHCOR$_6$ wherein the $C_{1-5}$ alkoxy may be substituted by OH, methoxy or halogen;
$R_6$ is independently hydrogen or $C_{1-4}$ alkyl;
$R_7$ is independently hydrogen, $C_{1-6}$ alkyl or (CH$_2$)$_n$Ar;
$R_8$ is hydrogen, $R_{11}$, CO$_2$H, PO$_3$H$_2$, P(O)(OH)R$_7$ or tetrazole;
$R_9$ is $C_{1-10}$ alkyl, $C_{2-10}$ alkenyl or phenyl all of which may be substituted by one or more OH, N(R$_6$)$_2$, COOH, halogen or XC$_{1-5}$ alkyl;
$R_{10}$ is $R_3$ or $R_4$;
$R_{11}$ is $C_{1-8}$ alkyl, $C_{2-8}$ alkenyl, $C_{2-8}$ alkynyl all of which may be substituted by one or more OH, CH$_2$OH, N(R$_6$)$_2$ or halogen;
X is (CH$_2$)$_n$, O, NR$_6$ or S(O)$_q$;
Y is CH$_3$ or —CH$_2$X(CH$_2$)$_n$Ar;
Ar is

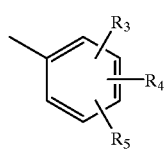

(a)

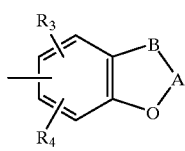

(b)

naphthyl, indolyl, pyridyl or thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be substituted by one or more R3 or R4 groups;
A is C=O, or [C(R$_6$)$_2$]$_m$;
B is —CH$_2$— or —O—;
$Z_1$ and $Z_2$ are independently hydrogen, $C_{1-8}$ alkyl, $C_{2-8}$ alkenyl, $C_{2-8}$ alkynyl, OH, $C_{1-8}$ alkoxy, S(O)$_q$C$_{1-8}$ alkyl, N(R$_6$)$_2$, Br, F, I, Cl, NHCOR$_6$, —X(CH$_2$)$_n$R$^8$, phenyl, benzyl or $C_{3-6}$ cycloalkyl wherein the $C_{1-8}$ alkyl, $C_{2-8}$ alkenyl or $C_{2-8}$ alkynyl may be optionally substituted by COOH, OH, CO(CH$_2$)$_n$CH$_3$, CO(CH$_2$)$_n$CH$_2$N(R$_6$)$_2$, or halogen; or $Z_1$ and $Z_2$ together may be —O—A—O— on contiguous carbons;
$Z_3$ is $Z_1$ or XR$_9$Y;
q is zero, one or two;
n is an integer from 0 to six;
m is 1, 2 or 3;
and the dotted line indicates the optional presence of a double bond; or a pharmaceutically acceptable salt thereof; provided that $R_2$ is not hydrogen when X is S(O)$_q$;
when the optional double bond is present there is only one $R_{10}$ and there is no $P_1$;
the compound of Formula I is not (1RS)-1,3-diphenylindene-2-carboxylic acid; (cis, cis)-(1RS, 3SR)-1,3-diphenylindane-2-carboxylic acid; (1RS)-3-[3-Methyl-1-phenyl-(1H)-ind-2-en-1-yl] propionic aicd; or (1RS)-2[1,3-diphenyl-(1H)-ind-2-en-2-yl] ethanoic acid.

Examples of chain peptides include the peptides described in Japanese Patent Unexamined Publication Nos. 244097/1992, 283600/1992 and WO93110144.
(1) Japanese Patent Unexamined Publication No. 244097/1992:
a peptide of the formula:

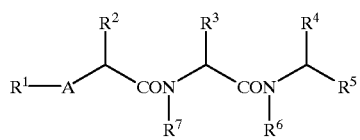

in which
$R^1$ is hydrogen or acyl,
$R^2$ is lower alkyl, optionally substituted ar(lower)alkyl, cyclo(lower)alkyl(lower)alkyl or optionally substituted heterocyclic(lower) alkyl,
$R^3$ is optionally substituted heterocyclic(lower)alkyl or optionally substituted ar(lower)alkyl,
$R^4$ is hydrogen or optionally substituted lower alkyl,
$R^5$ is carboxy, protected carboxy, carboxy(lower)alkyl or protected carboxy(lower)alkyl,
$R^6$ is hydrogen or optionally substituted lower alkyl,
$R^7$ is hydrogen or lower alkyl, and
A is —O—, —NH—, lower alkylimino or lower alkylene, provided that when $R^2$ is (S)-isobutyl, $R^3$ is N-(dichlorobenzyloxycarbonyl)indol-3-ylmethyl, $R^4$ is methyl, $R^5$ is methoxycarbonyl, $R^6$ is hydrogen, $R^7$ is hydrogen and A is —NH—, then the partial formula:

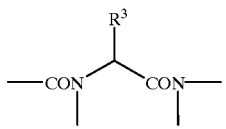

has the absolute configuration of

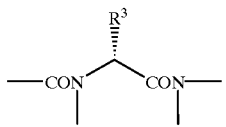

or a pharmaceutically acceptable salt thereof.

(2) Japanese Patent Unexamined Publication No. 283600/1992:

a peptide derivative represented by the formula:

wherein $X_1$ represents leucine, arginine or glutamine residue, $X_2$ represents isoleucine or valine residue, $X_3$ represents tryptophan, amidotryptophan or D-naphtylalanine residue and R1 represents residual 15 amino acids.

(3) WO93110144:

a compound of the formula:

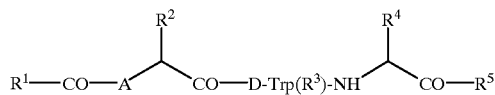

in which $R^3$ is hydrogen or lower alkyl, $R^4$ is pyridyl(lower)alkyl; and $R^1$ is $C_3$–$C_8$ alkyleneamino, N,N-di(lower)alkylamino, N-lower alkyl-N-arylamino, N-lower alkyl-N-$C_3$–$C_8$ cycloalkylamino, or $C_5$–$C_{10}$ bycyclic alkyleneamino, $R^2$ is lower alkyl, $R^5$ is $C_3$–$C_8$ alkyleneamino, N,N-di(lower)alkylamino, morpholino, thiomorpholino, N',N'-di(lower)alkylhydrazino, morpholinoamino, lower alkylpiperazinylamino, lower alkoxy(lower)alkylamino, morpholino(lower)alkylamino, $C_3$–$C_8$ alkyleneamino(lower)alkylamino which may be substituted by oxo, or pyridyl(lower)alkylamino, and A is lower alkylene; or $R^1$ is piperidin-1-yl, lower alkylpiperidin-1-yl, octahydroazocin-1-yl, indolin-1-yl, 1,2,3,4-tetrahydroquinolin-1-yl, N,N-di(lower)alkylamino, N-lower alkyl-N-arylamino, N-lower alkyl-N-$C_3$–$C_8$ cycloalkylamino, or $C_5$–$C_{10}$ bycyclic alkyleneamino, $R^2$ is lower alkyl, $R^5$ is amino or lower alkylamino, and A is lower alkylene; or $R^1$ is piperidin-1-yl, octahydroazocin-1-yl, N,N-di(lower)alkylamino, or $C_5$–$C_{10}$ bycyclic alkyleneamino, $R^2$ is lower alkyl, $R^5$ is amino, lower alkylamino, N,N-di(lower)alkylamino, $C_3$–$C_8$ alkyleneamino, or morpholino, and A is —NH—; or $R^1$ hexahydro-1H-azepin-1-yl, $R^2$ is isobutyl, $R^5$ is ethylamino, and A is methylene; or $R^1$ is N-[1-(dimethylcarbamoyl)-2,2-dimethylpropyl]amino, $R^2$ is isobutyl, $R^5$ is amino, and A is —NH—; or $R^1$ is N,N-di(lower)alkylamino, 1,2,3,4-tetrahydroquinolin-1-yl, N-lower alkyl-N-arylamino, or N-lower alkyl-N-$C_3$–$C_8$ cycloalkylamino, $R^2$ is lower alkyl, $R^5$ is hydroxy or CO—$R^5$ is protected carboxy, and A is lower alkylene; or $R^1$ is $C_5$–$C_{10}$ bycyclic alkyleneamino, $R^2$ is lower alkyl, $R^5$ is hydroxy or CO—$R^5$ is protected carboxy, and A is lower alkylene or —NH—; or $R^1$ is N-ethyl-N-(1-ethylpropyl)amino, N-ethyl-N-isopropylamino, N-ethyl-N-neopentylamino, or N-(1-ethylpropyl)-N-propylamino, $R^2$ is isobutyl, $R^5$ is hydroxy or CO—$R^5$ is protected carboxy, and A is —NH—; or $R^1$ is piperidin-1-yl, $R^2$ is isobutyl, $R^5$ is hydroxy or CO—$R^5$ is protected carboxy, and A is methylene; or $R^1$ is hexahydro-1H-azepin-1-yl, $R^2$ is propyl, $R^5$ is hydroxy or CO—$R^5$ is protected carboxy, and A is —NH—;

or a pharmaceutically acceptable salt thereof.

Examples of cyclic peptides include the peptides described in Japanese Patent Unexamined Publication No. 261198/1992.

Japanese Patent Unexamined Publication No. 261198/1992: a cyclic pentapeptide of the formula:

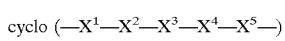

wherein $X^1$~$X^5$ represent amino acid residues, respectively, and $X^1$ is D—Phe, D—Tyr, D—Tha, D—Tza, D—Nal, D—Bta, D—Trp, D—Trp(O), D—Trp(CHO) or D—Trp$((CH_2)_mCOR^1$, wherein m is from 0 to 6, and $R^1$ is a hydroxyl group, a $C_1$–$C_6$ alkoxy group, an amino group or a $C_1$–$C_6$ monoalkylamino group, provided that when m=0, $R^1$ is not a hydroxyl group; $X^2$ is D—Asp, D—Glu, or D—Cys($O_3$H); $X^3$ is Pro, Hyp, Pip, Thz, β-Ala, Gly, Ala, α-Aba, Aib, Val, Nva, Leu, Ile, aIle, Nle, Met, Met(O), Met($O_2$), Phe, Tza, Tha, Tyr, Trp, His, Arg, Lys, Lys(CHO), Orn, Orn(O), Asn, Gln, Asp, Glu, Cys($O_3$H), Cys, Ser or Thr wherein those α-amino acids having a hydrogen atom on the α-amino group are optionally substituted by a $C_1$–$C_6$ alkyl or $C_3$–$C_7$ cycloalkyl group which optionally has a group selected from the group consisting of an imidazolyl group, a carboxyl group, a sulfo group and a hydroxy group; $X^4$ is D—Ala, D—Thr, D-α-Aba, D—Val, D—Nva, D—Leu, D—Ile, D—aIle, D—Nle, D—tert—Leu, D—Cpg, D—Chg, D—Dpg, D—Pen, Aib, $Ac_3c$, $Ac_4c$, $Ac_5c$, $Ac_6c$, $Ac_7c$, D—Phg, D—Thg, D—Fug, D—Tzg or D—Itg wherein those α-amino acids having a hydrogen atom at the α-position are optionally substituted by a $C_1$–$C_3$ alkyl group; $X^5$ is Pro, Pip, Thz, His, Ala, α-Aba, Val, Nva, Leu, Ile, aIle, Nle, Met, $C_3$al, $C_4$al, $C_5$al or $C_6$al wherein those α-amino acids having hydrogen atom on the α-amino group are optionally substituted by a $C_1$–$C_6$ alkyl group; or a pharmaceutically acceptable salt thereof.

Examples of cyclic and chain peptides-containing compounds include the peptides described in Japanese Patent Unexamined Publication No. 288099/1992.

Japanese Patent Unexamined Publication No. 288099/1992:

a peptide represented by the formula

Cys-Val-Xaa₁-Phe-Cys-His-Leu-Xaa₂-Ile-Ile-Xaa₃ wherein $Xaa_1$ represents Tyr, Phe or Ala, $Xaa_2$ represents Asp or Gly, $Xaa_3$ represents Trp or Phe.

The above-described endothelin antagonists include those produced by microbes, such as cochinmicins, a cyclodepsipeptide [The Journal of Antibiotics, Vol. 45, No. 11, 1709–1722 (1992)].

Examples of endothelin antagonists which antagonize both receptors ET-A and ET-B include the cyclic peptide (I) described hereinafter which is described in European Patent Publication No. 528312 and Japanese Patent Application No. 27872211993.

More specifically, the anti-endothelin substance in the present invention is preferably a peptide represented by the general formula:

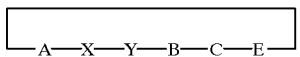

[I]

—A—X—Y—B—C—E— wherein X and Y independently represent an α-amino acid residue; A represents a D-acidic-α-amino acid residue; B represents a neutral-α-amino acid residue; C represents an L-α-amino acid residue; E represents a D-α-amino acid residue having an aromatic cyclic group.

With respect to general formula [I], the parent amino acid for the α-amino acid residue represented by X or Y may be any amino acid, as long as it is an α-amino acid. Such amino acids include alanine, arginine, asparagine, aspartic acid, cysteine, glutamine, glutamic acid, 2-aminomalonic acid, 2-aminoadipic acid, glycine, histidine, isoleucine, leucine, lysine, ornithine, 2,4-diaminobutyric acid, Methionine, phenylalanine, proline, 4-hydroxyproline, thioproline, azetidine-2-carboxylic acid, pipecolic acid (piperidine-2-carboxylic acid), indoline-2-carboxylic acid, tetrahydroisoquinoline-3-carboxylic acid, serine, threonine, tryptophan, 5-methyltryptophan, tyrosine, valine, alloisoleucine, norvaline, norleucine, tertiary leucine, gamma methylleucine, phenylglycine, 2-aminobutyric acid, cysteic acid, homocysteic acid, 1-naphthylalanine, 2-naphthylalanine, 2-thienylglycine, 3-thienylglycine, 3-benzothienylalanine, 4-biphenylalanine, pentamethylphenylalanine, 1-aminocyclopropane-1-carboxylic acid, 1-aminocyclobutane-1-carboxylic acid, 1-aminocyclopentane-1-carboxylic acid, 1-aminocyclohexane-1-carboxylic acid and 1-aminocycloheptane-1-carboxylic acid. When these α-amino acids have functional groups (e.g., hydroxyl group, thiol group, amino group, imino group and carboxyl group), the functional groups may be substituted for by a suitable substituent.

Hydroxyl groups which are substituted include $C_{1-6}$ alkanoyloxy (e.g., formyloxy, acetoxy and propionyloxy), $C_{4-9}$ alicyclic carbonyloxy (e.g., cyclopentanecarbonyloxy and cyclohexanecarbonyloxy), $C_{7-15}$ arylcarbonyloxy (e.g., benzoyloxy and 4-methylbenzoxloxy), $C_{8-16}$ aralkylcarbonyloxy (e.g., phenylacetoxy, 2-phenylpropionyloxy, 3-phenylpropionyloxy and diphenylacetoxy), aromatic heterocyclic-alkylcarbonyloxy (e.g., indol-2-ylacetoxy and indol-3-ylacetoxy), $C_{1-6}$ alkoxy (e.g., methoxy, ethoxy, n-propoxy and tert-butoxy), $C_{3-8}$ cycloalkoxy (e.g., cyclopentoxy and cyclohexyloxy), $C_{6-12}$ aryloxy (e.g., phenyloxy and 4-methylphenyloxy) and $C_{7-15}$ aralkyloxy (e.g., benzyloxy, phenethyloxy and diphenylmethoxy). α-Amino acids in which hydroxyl group is substituted include o-acetylserine, o-acetylthreonine, 4-acetoxyproline, o-benzoylserine, o-benzoylthreonine, 4-benzoyloxyproline, o-phenylacetylserine, o-phenylacetylthreonine, 4-phenylacetoxyproline, o-ethylserine, o-ethylthreonine, 4-ethoxyproline, o-cyclohexylserine, o-cyclohexylthreonine, 4-cyclohexyloxyproline, o-phenylserine, o-phenylthreonine, 4-phenoxyproline, o-benzylserine, o-benzylthreonine, 4-benzyloxyproline, o-diphenylmethylserine, o-diphenylmethylthreonine and 4-diphenylmethoxyproline.

Thiol groups which are substituted include $C_{1-6}$ alkanoylthio (e.g., formylthio, acetylthio and propionylthio), $C_{4-9}$ alicyclic carbonythio (e.g., cyclopentanecarbonylthio and cyclohexanecarbonylthio), $C_{7-15}$ arylcarbonylthio (e.g., benzoylthio and 4-methylbenzoylthio), $C_{8-16}$ aralkylcarbonylthio (e.g., phenylacetylthio, 2-phenylpropionylthio, 3-phenylpropionylthio and diphenylacetylthio), $C_{1-6}$ alkylthio (e.g., methylthio, ethylthio, n-propylthio and tert-butylthio), $C_{3-8}$ cycloalkylthio (e.g., cyclopentylthio and cyclohexylthio), $C_{6-12}$ arylthio (e.g., phenylthio and 4-methylphenylthio) and $C_{7-15}$ aralkylthio (e.g., benzylthio, phenethylthio and diphenylmethylthio). α-Amino acids in which thiol group is substituted include S-acetylcysteine, S-benzoylcysteine, S-phenylacetylcysteine, S-ethylcysteine, S-cyclohexylcysteine, S-phenylcysteine and S-benzylcysteine.

Amino groups which are substituted include $C_{1-6}$ alkylamino (e.g., N-methylamino, N-ethylamino and N-tert-butylamino), $C_{3-8}$ cycloalkylamino (e.g., N-cyclopentylamino and N-cyclohexylamino ), $C_{6-12}$ arylamino (e.g., N-phenylamino and N-{4-methyl phenyl}amino), $C_{7-15}$ aralkylanmino (e.g., N-benzylamino, N-phenethylamino, N-{2-chlorobenzyl}amino, N-{3-chlorobenzyl}amino, N-{4-chlorobenzyl}amino, N-{2-methylbenzyl}amino, N-{3-methylbenzyl}amino, N-{4-methylbenzyl}amino, N-{2-methoxybenzyl}amino, N-{3-methoxybenzyl}amino and N-{4-methoxybenzyl}amino), aromatic heterocyclic-$C_{1-6}$ alkylamino (e.g., 2-furylmethylamino, 3-furylmethylamino, 2-thienylmethylamino, 3-thienylmethylamino, indol-2-ylmethylamino and indol-3-ylmethylamino), and $C_{1-6}$ aliphatic acylamido (e.g., formamido, acetamido and propionamido), $C_{4-9}$ alicyclic acylamido (e.g., cyclopentanecarboxamido and cyclohexanecarboxamido), $C_{7-15}$ arylacylamido (e.g., benzamido and 4-methylbenzamido), $C_{8-16}$ aralkylacylamido (e.g., phenylacetamido, 2-phenylpropionamido, 3-phenylpropionamido, diphenylacetamido, 1-naphthylacetamido and 2-naphthylacetamido), aromatic heterocyclic-carboxamido (e.g., indol-2-ylcarboxamido and indol-3-ylcarboxamido), aromatic heterocyclic-alkylcarboxamido(e.g., indol-2-ylacetamido and indol-3-ylacetamido), and sulfonylamido (e.g., benzenesulfonylamido, p-toluenesulfonylamido and 4-methoxy-2,3,6-trimethylbenzenesulfonylamido). Substituents in imino or imido groups which are substituted are the same as those in each amino or amido groups which are substituted. α-Amino acids wherein the amino group is substituted include N-methylglycine (sarcosine), N-ethylglycine, N-methylleucine, N-ethylleucine, N-methylphenylalanine, N-ethylphenylalanine, N(α)-methyltryptophan, N(α)-ethyltryptophan, N-cyclopentylglycine, N-cyclohexylglycine, N-phenylglycine, N-phenylleucine, N-benzylglycine, N-benzylleucine, N(n)-benzylhistidine, N(τ)-benzylhistidine, N(π)-phenacylhistidine, N(π)-benzyloxymethylhistidine, $N^g$-benzenesulfonylarginine, $N^g$-p-toluenesulfonylarginine, $N^g$-(4-methoxy-2,3,6-trimethylbenzenesulfonyl)arginine, N(ε)-benzenesulfonyllysine, N(ε)-p-toluenesulfonyllysine, N(ε)-(4-methoxy-2,3,6-trimethylbenzenesulfonyl) lysine, $N^{in}$-methyltryptophan, $N^{in}$-ethyltryptophan, $N^{in}$-formyltryptophan, $N^{in}$-acetyltryptophan, N(ε)-benzyllysine, N(ε)-(2-furylmethyl)lysine, N(ε)-(2-thienylmethyl)lysine, N(ε)-(indol-3-ylmethyl)lysine, N(ε)-phenylacetyl)lysine, N(ε)-({2-furyl}acetyl)lysine, N(ε)-({2-thienyl}acetyl) lysine, N(ε)-({indol-3-yl}acetyl)lysine, N(ε)-benzoyllysine, N(ε)-(3-phenylpropionyl)lysine, N(δ)-benzylornithine, N(δ)-(2-furylmethyl)ornithine, N(δ)-(2-thienylmethyl) ornithine, N(δ)-(indol-3-ylmethyl)ornithine, N(δ)-benzoylornithine, N(δ)-phenylacetylornithine, N(δ)-(3-phenylpropionyl)ornithine, N(δ)-({2-methylphenyl}acetyl)) ornithine, N(δ)-({3-methylphenyl}acetyl)ornithine, N(δ)-({4-methylphenyl}acetyl) ornithine, N(δ)-({2-chlorophenyl}acetyl)ornithine, N(δ)-({3-chlorophenyl}acetyl)ornithine, N(δ)-({4-chlorophenyl}acetyl)ornithine, N(δ)-({2-methoxyphenyl}acetyl)ornithine, N(δ)-({3-methoxyphenyl}acetyl)ornithine, N(δ)-({4-methoxyphenyl}acetyl)ornithine, N(δ)-(4-biphenylacetyl) ornithine, N(γ)-benzyl-2,4-diaminobutyric acid, N(γ)-(2-furylmethyl)-2,4-diaminobutyric acid, N(γ)-(2-thienylmethyl)-2,4-diaminobutyric acid, N(γ)-(indol-3-ylmethyl)-2,4-diaminobutyric acid, N(γ)-benzoyl-2,4-diaminobutyric acid, N(γ)-phenylacetyl-2,4-diaminobutyric acid, N(γ)-(3-phenylpropionyl)-2,4-diaminobutyric acid, N(γ)-(2-furylacetyl)-2,4-diaminobutyric acid, N(γ)-(2-thienylacetyl)-2,4-diaminobutyric acid and N(γ)-({indol-3-yl}acetyl)-2,4-diaminobutyric acid.

Carboxyl groups which are substituted include carbamoyl group (—$CONH_2$) and substituted carbamoyl group such as N—$C_{1-6}$ alkylcarbamoyl (e.g., methylcarbamoyl, ethylcarbamoyl, n-propylcarbamoyl and tert-butylcarbamoyl), $C_{3-8}$ cycloalkylcarbamoyl (e.g., cyclopentylcarbamoyl and cyclohexylcarbamoyl), $C_{6-12}$ arylcarbamoyl (e.g., phenylcarbamoyl and 4-methylphenylcarbamoyl), $C_{7-15}$ aralkylcarbamoyl (e.g., benzylcarbamoyl, phenetyl and 1,2-diphenylethylcarbamoyl), aromatic heterocyclic-$C_{1-6}$ alkylcarbamoyl (e.g., 2-{indol-2-yl}ethylcarbamoyl and 2-{indol-3-yl}ethylcarbamoyl), piperidinocarbonyl, piperazincarbonyl, $N^4$-$C_{1-6}$ alkylpiperazincarbonyl (e.g., $N^4$-methylpiperazincarbonyl and $N^4$-ethylpiperazincarbonyl), $N^4$-$C_{3-8}$ cycloalkylpiperazincarbonyl (e.g., $N_4$-cyclopentylpiperazincarbonyl and $N^4$-cyclohexylpiperazincarbonyl), $N^4$-5 to 7-membered heterocyclic piperazincarbonyl (e.g., $N^4$-pyridylpiperazincarbonyl, $N^4$-furylpiperazincarbonyl and $N^4$-thienylpiperazincarbonyl), $N^4$-$C_{6-12}$ arylpiperazincarbonyl (e.g., $N^4$-phenylpiperazincarbonyl and $N^4$-{4-methylphenyl}piperazincarbonyl), $N^4$-$C_{7-15}$ aralkylpiperazincarbonyl (e.g., $N^4$-benzylpiperazincarbonyl, $N^4$-phenetylpiperazincarbonyl and $N^4$-{1,2-diphenylethyl}piperazincarbonyl), $N^4$-{aromatic heterocyclic -$C_{1-6}$ alkyl}piperazincarbonyl (e.g., $N^4$-[2-{indol-2-yl}ethyl]piperazincarbonyl and $N^4$-[2-{indol-3-yl}ethyl] piperazincarbonyl), $N^4$-$C_{1-6}$ aliphatic acylpiperazincarbonyl (e.g., $N^4$-acetylpiperazincarbonyl and $N^4$-propionylpiperazincarbonyl), $N^4$-$C_{4-9}$ alicyclic acylpiperazincarbonyl (e.g., $N^4$-cyclopentanecarbonylpiperazincarbonyl and $N^4$-cyclohexane carbonylpiperazincarbonyl), $N_4$-$C_{7-15}$ arylacylpiperazincarbonyl (e.g., $N^4$-benzoylpiperazincarbonyl and $N^4$-{4-methylbenzoyl}piperazincarbonyl), $N^4$-$C_{8-16}$ aralkylacylpiperazincarbonyl (e.g., $N^4$-phenylacetylpiperazincarbonyl, $N^4$-{2-phenylpropion}piperazincarbonyl, $N^4$-{3-phenylpropionyl}piperazincarbonyl, $N^4$-diphenylacetylpiperazincarbonyl, $N^4$-{1-naphthylacetyl}piperazincarbonyl and $N^4$-{2-naphthylacetyl}piperazincarbonyl), $N^4$-{aromatic heterocyclic-carbonyl}piperazincarbonyl (e.g., $N^4$-{indol-2-ylcarbonyl}piperazincarbonyl and $N^4$-{indol-3-ylcarbonyl}piperazincarbonyl) and $N^4$-{aromatic heterocyclic-alkylcarbonyl}piperazincarbonyl (e.g., $N^4$-{indol-2-ylacetyl}piperazincarbonyl and $N^4$-{indol-3-ylacetyl}piperazincarbonyl), and $C_{1-6}$ alkyloxycarbonyl (e.g., methoxycarbonyl, ethoxycarbonyl and n-propoxycarbonyl), $C_{3-8}$ cycloalkyloxycarbonyl (e.g., cyclopentyloxycarbonyl and cyclohexyloxycarbonyl) and $C_{7-15}$ aralkyloxycarbonyl (e.g., benzyloxycarbonyl, phenethyloxycarbonyl, 1-phenylethoxycarbonyl and diphenylmethoxycarbonyl). The above substituted carbamoyl groups include amides with α-amino acids and amides with oligopeptides (e.g., dipeptide, tripeptide and tetrapeptide). α-amino acids wherein the carboxyl group is substituted include $N^4$-methylasparagine, $N^4$-phenylasparagine, $N^4$-benzylasparagine, $N^4$-phenetylasparagine, $N^4$-(2-{indol-3-yl}ethyl) asparagine, $N^5$-methylglutamine, $N^5$-phenylglutamine, $N^5$-benzylglutamine, $N^5$-phenetylglutamine, $N^5$-(2-{indol-3-yl}ethyl)glutamine, aspartic acid β-methyl ester, aspartic acid β-cyclopropyl ester, aspartic acid β-benzyl ester, aspartic acid β-phenethyl ester, aspartic acid β-$N^4$-phenylpiperazinamide, aspartic acid β-$N^4$-(2-methylphenyl) piperazinamide, aspartic acid β-$N^4$-(3-methylphenyl) piperazinamide, aspartic acid β-N'-(4-methylphenyl) piperazinamide, aspartic acid β-$N^4$-(2-methoxyphenyl) piperazinamide, aspartic acid β-$N^4$-(3-methoxyphenyl) piperazinamide, aspartic acid β-$N^4$-(4-methoxyphenyl) piperazinamide, aspartic acid β-$N^4$-(2-chlorophenyl) piperazinamide, aspartic acid β-$N^4$-(3-chlorophenyl) piperazinamide, aspartic acid β-$N^4$-(4-chlorophenyl) piperazinamide, aspartic acid β-$N^4$-(4-nitrophenyl) piperazinamide, aspartic acid β-$N^4$-(4-fluorophenyl) piperazinamide, aspartic acid β-$N^4$-(3-trifluoromethylphenyl)piperazinamide, aspartic acid β-$N^4$-(2,3-dimethylphenyl)piperazinamide, aspartic acid β-$N^4$-(2-pyridyl)piperazinamide, aspartic acid β-$N^4$-(2-pyrimidyl) piperazinamide, glutamic acid γ-methyl ester, glutamic acid γ-cyclopropyl ester, glutamic acid γ-benzyl ester and glutamic acid γ-phenethyl ester.

With respect to general formula [I], the parent α-amino acid for the α-amino acid residue represented by X or Y may be any isomer, whether D, L or DL, with preference given to the L-isomer for both X and Y.

X preferably represents —Asp($R^1$)—. —Asp($R^1$)— is a group of the formula:

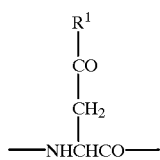

wherein $R^1$ represents a group represented by the formula:

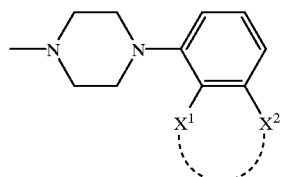

wherein $X^1$ and $X^2$ independently represent a hydrogen atom, $C_{1-6}$ alkyl group, $C_{1-6}$ alkoxy group, a halogen atom or a nitro group, and $X^1$ and $X^2$ independently may be combined together to form a ring in

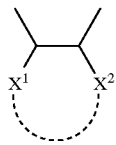

Examples of $C_{1-6}$ alkyl group represented by $X^1$ and $X^2$ are methyl, ethyl, n-propyl, iso-propyl, n-butyl, iso-butyl, tert-butyl, n-pentyl and n-hexyl, among which $C_{1-3}$ alkyl group such as methyl, ethyl, n-propyl and iso-propyl is preferred. Most preferred is methyl.

Examples of $C_{1-6}$ alkoxy group represented by $X^1$ and $X^2$ are methoxy, ethoxy, n-propoxy, n-butoxy, n-pentyloxy and n-hexyloxy, among which $C_{1-3}$ alkoxy group such as methoxy, ethoxy and n-propoxy is preferred. Most preferred is methoxy or ethoxy.

Examples of halogen atom represented by $X^1$ and $X^2$ are fluorine, chlorine, bromine and iodine, among which chlorine is preferred.

Examples of $R^1$ in case $X^1$ and $X^2$ are combined together to form a ring are represented by the formula;

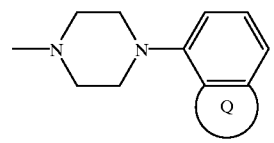

Examples of ring Q are 4 to 7-membered rings which may contain 1 to 3 hetero atom selected from O, N or S (e.g. saturated carbon rings, aromatic carbon rings, saturated heterocyclic rings and aromatic heterocyclic rings).

$R^1$ is preferably represented by the formula;

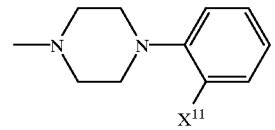

wherein $X^{11}$ represents a hydrogen atom, $C_{1-6}$ alkyl group, $C_{1-6}$ alkoxy group, a halogen atom or a nitro group.

Preferred examples of $R^1$ are

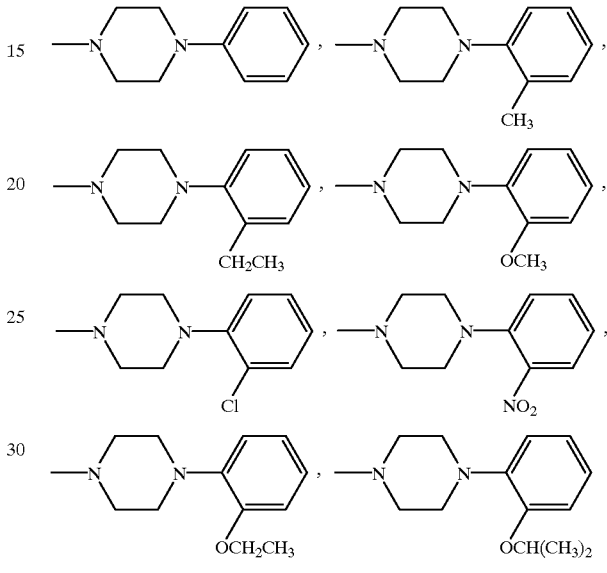

Above mentioned —Asp($R^1$)— may be any isomer, whether D, L or DL, with preference given to L-isomer.

With respect to general formula [I], the parent amino acid for the D-acidic-α-amino acid residue represented by A is exemplified by amino acids having an acidic group such as the carboxyl group, sulfo group or tetrazolyl group in the side chain thereof, including D-glutamic acid, D-aspartic acid, D-cysteic acid, D-homocysteic acid, D-β-(5-tetrazolyl) alanine and D-2-amino-4-(5-tetrazolyl)butyric acid, with preference given to D-glutamic acid, D-aspartic acid and D-cysteic acid.

With respect to general formula [I], the parent amino acid for the neutral-α-amino acid residue represented by B is exemplified by α-amino acids such as alanine, valine, norvaline, leucine, isoleucine, alloisoleucine, norleucine, tert-leucine, γ methylleucine, phenylglycine, phenylalanine, 1-naphthylalanine, 2-naphthylalanine, proline, 4-hydroxyproline, azetidine-2-carboxylic acid, pipecolic acid (piperidine-2-carboxylic acid), 2-thienylalanine, 2-thienylglycine, 3-thienylglycine, 1-aminocyclopropane-1-carboxylic acid, 1-aminocyclobutane-1-carboxylic acid, 1-aminocyclopentane-1-carboxylic acid, 1-aminocyclohexane-1-carboxylic acid, 1-aminocycloheptane-1-carboxylic acid, 2-cyclopentylglycine and 2-cyclohexylglycine. If the neutral-α-amino acid involves both the L- and D-configurations, the D-configuration is preferred. Greater preference is given to D-leucine, D-alloisoleucine, D-tert-leucine, D-γ methylleucine, D-phenylglycine, D-2-thienylalanine, D-2-thienylglycine, D-3-thienylglycine and D-2-cyclopentylglycine. The α-amino group of these neutral-α-amino acids may be replaced by a $C_{1-6}$ alkyl group (e.g., methyl, ethyl, n-propyl or tert-butyl). Such α-amino acids include N-methylleucine, N-methylalloisoleucine, N-methyl tert-leucine, N-methyl γ methylleucine and N-methylphenylglycine, preferably of the D-configuration.

B preferably represents —NH—CHR$^2$—CO—, wherein R$^2$ represents $C_{1-6}$ alkyl group, $C_{3-7}$ cycloalkyl group, $C_{3-7}$ cycloalkyl-$C_{1-3}$ alkyl group, $C_{1-6}$ alkylthio-$C_{1-3}$ alkyl group, $C_{3-7}$ cycloalkylthio-$C_{1-3}$ alkyl group, $C_{1-6}$ alkoxy-$C_{1-3}$ alkyl group, $C_{3-7}$ cycloalkoxy-$C_{1-3}$ alkyl group, $C_{1-6}$ alkylthio group, $C_{3-7}$ cycloalkylthio group, $C_{1-6}$ alkoxy group or $C_{3-7}$ cycloalkoxy group.

Examples of $C_{1-6}$ alkyl group represented by R$^2$ are methyl, ethyl, n-propyl, iso-propyl, n-butyl, iso-butyl, (1-methyl) propyl, tert-butyl, n-pentyl, (2-methyl) butyl, (3-methyl) butyl, neopentyl, n-hexyl, (2,2-dimethyl) butyl and (3,3-dimethyl) butyl, among which $C_{4-6}$ alkyl group such as n-butyl, iso-butyl, (1-methyl) propyl, tert-butyl, n-pentyl, (2-methyl) butyl, (3-methyl) butyl, (2-methyl) butyl, (3-methyl) butyl, neopentyl and n-hexyl is preferred.

Examples of $C_{3-7}$ cycloalkyl group represented by R$^2$ are cyclopropyl, cyclobutyl, cyclopentyl, cyclohexyl and cycloheptyl, among which $C_{5-7}$ cycloalkyl group such as cyclopentyl, cyclohexyl and cycloheptyl is preferred.

Examples of $C_{3-7}$ cycloalkyl-$C_{1-3}$ alkyl group represented by R$^2$ are cyclopropylmethyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, cycloheptylmethyl and cycloheptylethyl, among which $C_{3-7}$ cycloalkyl-methyl group such as cyclopropylmethyl, cyclobutylmethyl, cyclopentylmethyl, cyclohexylmethyl, cycloheptylmethyl is preferred.

Examples of $C_{1-6}$ alkylthio-$C_{1-3}$ alkyl group represented by R$^2$ are methylthiomethyl, methylthioethyl, methylthiopropyl, ethylthiomethyl, ethylthioethyl, n-propylthiopropyl, iso-propylthiomethyl, n-butylthiomethyl, tert-butylthiomethyl, n-butylthioethyl, tert-butylthiopropyl and (1,1-dimethyl) propylthiomethyl, among which $C_{3-7}$ alkylthio-methyl group such as iso-propylthiomethyl, n-butylthiomethyl, tert-butylthiomethyl and (1,1-dimethyl) propylthiomethyl is preferred.

Examples of $C_{3-7}$ cycloalkylthio-$C_{1-3}$ alkyl group represented by R$^2$ are cyclopropylthiomethyl, cyclopropylthioethyl, cyclopropylthiopropyl, cyclobutylthiomethyl, cyclobutylthioethyl, cyclobutylthiopropyl, cyclopentylthiomethyl, cyclopentylthioethyl, cyclohexythiomethyl and cycloheptylthiomethyl, among which $C_{4-7}$ cycloalkylthiomethyl group such as cyclobutylthiomethyl, cyclopentylthiomethyl, cyclohexylthiomethyl and cycloheptylthiomethyl is preferred.

Examples of $C_{1-6}$ alkoxy-$C_{1-3}$ alkyl group represented by R$^2$ are methoxymethyl, methoxyethyl, methoxypropyl, ethoxymethyl, ethoxyethyl, n-propoxymethyl, n-propoxyethyl, iso-propoxymethyl, iso-propoxyethyl, n-butoxymethyl, n-butoxyethyl, tert-butoxymethyl, tert-butoxyethyl, n-pentyloxymethyl, n-pentyloxyethyl, (1,1-dimethyl) propoxymethyl, (1,1-dimethyl) propoxyethyl, n-hexyloxymethyl and n-hexyloxyethyl, among which $C_{1-6}$ alkoxy-methyl group such as methoxymethyl, ethoxymethyl, n-propoxymethyl, iso-propoxymethyl, n-butoxymethyl, tert-butoxymethyl, n-pentyloxymethyl, (1,1-dimethyl) propoxymethyl and n-hexyloxymethyl is preferred. More preferred are iso-propoxymethyl, tert-butoxymethyl, (1,1-dimethyl) propoxymethyl and n-hexyloxymethyl.

Examples of $C_{3-7}$ cycloalkoxy-$C_{1-3}$ alkyl group represented by R$^2$ are cyclopropoxymethyl, cyclopropoxyethyl, cyclobutoxymethyl, cyclobutoxyethyl, cyclopentyloxymethyl, cyclopentyloxyethyl, cyclohexyloxymethyl and cycloheptyloxymethyl, among which $C_{3-7}$ cycloalkoxy-methyl group such as cyclopropoxymethyl, cyclobutoxymethyl, cyclopentyloxymethyl, cyclohexyloxymethyl and cycloheptyloxymethyl is preferred.

Examples of $C_{1-6}$ alkylthio group represented by R$^2$ are methylthio, ethylthio, n-propylthio, iso-propylthio, n-butylthio, tert-butylthio, n-pentylthio, (1,1-dimethyl) propylthio and n-hexylthio, among which $C_{3-6}$ alkylthio group such as n-propylthio, iso-propylthio, n-butylthio, tert-butylthio, n-pentylthio, (1,1-dimethyl) propylthio and n-hexylthio is preferred.

Examples of $C_{3-7}$ cycloalkylthio group represented by R$^2$ are cyclopropylthio, cyclobutylthio, cyclopentylthio, cyclohexylthio and cycloheptylthio, among which $C_{4-7}$ cycloalkylthio group such as cyclobutylthio, cyclopentylthio, cyclohexylthio and cycloheptylthio is preferred.

Examples of $C_{1-6}$ alkoxy group represented by R$^2$ are methoxy, ethoxy, n-propoxy, iso-propoxy, n-butoxy, tert-butoxy, n-pentyloxy, (1,1-dimethyl) propoxy and n-hexyloxy, among which $C_{3-6}$ alkoxy group such as n-propoxy, iso-propoxy, n-butoxy, tert-butoxy, n-pentyloxy, (1,1-dimethyl) propoxy and n-hexyloxy is preferred.

Examples of $C_{3-7}$ cycloalkoxy group represented by R$^2$ are cyclopropoxy, cyclobutoxy, cyclopentyloxy, cyclohexyloxy and cycloheptyloxy, among which $C_{4-7}$ cycloalkoxy group such as cyclobutoxy, cyclopentyloxy, cyclohexyloxy and cycloheptyloxy is preferred.

R$^2$ is preferably $C_{1-6}$ alkyl group, more preferably $C_{4-6}$ alkyl group such as n-butyl, iso-butyl, (1-methyl) propyl, tert-butyl, n-pentyl, (2-methyl) butyl, (3-methyl) butyl, neopentyl and n-hexyl, with greater preference is given to tert-butyl and neopentyl.

Above mentioned α-amino acid represented by —NH—CHR$^2$—CO— may be any isomer, whether D, L or DL, with preference given to D-isomer.

With respect to general formula [I], the parent amino acid for the L-α-amino acid residue represented by C is exemplified by commonly known L-α-amino acids such as glycine, L-alanine, L-valine, L-norvaline, L-leucine, L-isoleucine, L-tert-leucine, L-norleucine, L-methionine, L-2-aminobutyric acid, L-serine, L-threonine, L-phenylalanine, L-aspartic acid, L-glutamic acid, L-asparagine, L-glutamine, L-lysine, L-tryptophan, L-arginine, L-tyrosine and L-proline, with preference given to L-leucine, L-norleucine and L-tryptophan. The α-amino group of these L-α-amino acids may be replaced by a $C_{1-6}$ alkyl group (e.g., methyl, ethyl, n-propyl or tert-butyl). Such L-α-amino acids include L-N-methylleucine, L-N-methylnorleucine and L-N(α)-methyltryptophan.

With respect to general formula [I], the parent amino acid for the D-α-amino acid residue having an aromatic cyclic group represented by E is exemplified by D-α-amino acids having an aromatic cyclic group in the side chain thereof. Examples of such amino acids include D-tryptophan, D-5-methyltryptophan, D-phenylalanine, D-tyrosine, D-1-naphthylalanine, D-2-naphthylalanine, D-3-benzothienylalanine, D-4-biphenylalanine and D-pentamethyl phenylalanine, with preference given to D-tryptophan and D-5-methyltryptophan. D-tryptophan is more preferred. The α-amino group of these D-α-amino acids having an aromatic ring may be replaced by a $C_{1-6}$ alkyl group (e.g., methyl, ethyl, n-propyl or tert-butyl). The amino group of the indole ring of D-tryptophan may be replaced by a hydrocarbon group such as a $C_{1-6}$ alkyl (e.g., methyl, ethyl, n-propyl or tert-butyl), $C_{3-8}$ cycloalkyl (e.g., cyclopentyl or cyclohexyl), $C_{6-12}$ aryl (e.g., phenyl or 4-methylphenyl) or $C_{7-15}$ aralkyl (e.g., benzyl or phenethyl) or by an acyl group such as a $C_{1-6}$ aliphatic acyl (e.g., formyl, acetyl or propionyl), $C_{4-9}$ alicyclic acyl (e.g., cyclopentanecarbonyl or cyclohexanecarbonyl), $C_{7-15}$ arylacyl (e.g., benzoyl or 4-methylbenzoyl), $C_{8-16}$ aralkylacyl (e.g., phenylacetyl, 2-phenylpropionyl, 3-phenylpropionyl or diphenylacetyl) or $C_{1-6}$ alkoxycarbonyl (e.g., methoxycarbonyl or ethoxycarbonyl). Such α-amino acids include D-N(α)-methyltryptophan, D-N-methylphenylalanine, D-N-methyltyrosine, D-$N^{in}$-methyltryptophan, D-$N^{in}$-ethyltryptophan, D-$N^{in}$-formyltryptophan and D-$N^{in}$-acetyltryptophan. D-$N^{in}$-methyltryptophan, D-$N^{in}$-formyltryptophan and D-$N^{in}$-acetyltryptophan are preferred.

E preferably represents Trp ($N^{in}$-$R^3$), wherein $R^3$ represents a hydrogen atom, $C_{1-6}$ alkyl group, $C_{3-7}$ cycloalkyl group, —$COR^4$ ($R^4$ represents a hydrogen atom, $C_{1-6}$ alkyl group, $C_{6-15}$ aryl group or $C_{6-15}$ aryl-$C_{1-3}$ alkyl group), —$COOR^5$ ($R^5$ represents $C_{1-6}$ alkyl group, $C_{6-15}$ aryl group or $C_{6-15}$ aryl-$C_{1-3}$ alkyl group) or —$CONHR^6$ ($R^6$ represents a hydrogen atom, $C_{1-6}$ alkyl group, $C_{6-15}$ aryl group or $C_{6-15}$ aryl-$C_{1-3}$ alkyl group) and $R^3$ is directly combined with N atom of indole group in tryptophan residue.

Examples of $C_{1-6}$ alkyl group represented by $R^3$ are methyl, ethyl, n-propyl, iso-propyl, n-butyl, iso-butyl, (1-methyl) propyl, tert-butyl, n-pentyl, (2-methyl) butyl, (3-methyl) butyl, neopentyl, n-hexyl, (2,2-dimethyl) butyl and (3,3-dimethyl) butyl, among which $C_{1-3}$ alkyl group such as methyl, ethyl, n-propyl and iso-propyl is preferred.

Examples of $C_{3-7}$ cycloalkyl group represented by $R^3$ are cyclopropyl, cyclobutyl, cyclopentyl, cyclohexyl and cycloheptyl, among which $C_{5-7}$ cycloalkyl group such as cyclopentyl, cyclohexyl and cycloheptyl is preferred.

Examples of $C_{1-6}$ alkyl group represented by $R^4$, $R^5$ and $R^6$ are methyl, ethyl, n-propyl, iso-propyl, n-butyl, iso-butyl, (1-methyl) propyl, tert-butyl, n-pentyl, (2-methyl) butyl, (3-methyl) butyl, neopentyl, n-hexyl, (2,2-dimethyl) butyl and (3,3-dimethyl) butyl, among which $C_{1-3}$ alkyl group such as methyl, ethyl, n-propyl and iso-propyl is preferred.

Examples of $C_{6-15}$ aryl group represented by $R^4$, $R^5$ and $R^6$ are phenyl, α-naphthyl and β-naphthyl, among which phenyl is preferred.

Examples of $C_{6-15}$ aryl-$C_{1-3}$ alkyl group represented by $R^4$, $R^5$ and $R^6$ are benzyl, phenylethyl, phenylpropyl, α-naphthylmethyl, α-naphthylethyl, α-naphthylpropyl, β-naphthylmethyl, β-naphthylethyl, β-naphthylpropyl, among which $C_{6-15}$ aryl-methyl group such as benzyl, α-naphthylmethyl and β-naphthylmethyl, is preferred.

Specific embodiment of —$COR^4$ is exemplified by formyl, acetyl, propionyl, butyryl, isobutyryl, isovaleryl, pivaloyl, n-benzylcarbonyl, benzoyl and phenylacetyl.

Specific embodiment of —$COOR^5$ is exemplified by methoxycarbonyl, ethoxycarbonyl, phenoxycarbonyl and benzyloxycarbonyl.

Specific embodiment of —$CONHR^6$ is exemplified by carbamoyl, methylaminocarbonyl, ethylaminocarbonyl, n-propylaminocarbonyl, iso-propylaminocarbonyl, n-butylaminocarbonyl, iso-butylaminocarbonyl, phenylaminocarbonyl and benzylaminocarbonyl.

$R^3$ is preferably a hydrogen atom and —$COR^4$ ($R^4$ represents a hydrogen atom, $C_{1-6}$ alkyl group, $C_{6-15}$ aryl group or $C_{6-15}$ aryl-$C_{1-3}$ alkyl group), with greater preference is given to a hydrogen atom, formyl and acetyl.

In the hexapeptide represented by general formula [I], or a salt thereof followings are preferred:

X is an the L-isomer; Y is an L-isomer; A is selected from the group consisting of D-glutamic acid, D-aspartic acid, D-cysteic acid and D-tetrazolylalanine residues; B is of the D-configuration; B is selected from the group consisting of 1-aminocyclopropane-1-carboxylic acid, 1-aminocyclobutane-1-carboxylic acid, 1-aminocyclopentane-1-carboxylic acid, 1-aminocyclohexane-1-carboxylic acid and 1-aminocycloheptane-1-carboxylic acid; B is selected from the group consisting of D-leucine, D-alloisoleucine, D-tert-leucine, D-γ methyl leucine, D-phenylglycine, D-2-thienylglycine, D-3-thienylglycine, D-2-cyclopentylglycine, D-phenylalanine, D-2-thienylalanine, D-valine, D-2-furylglycine and D-3-furylglycine residues; C is selected from the group consisting of L-leucine, L-isoleucine, L-valine, L-norleucine and L-α-amino acid residues having an aromatic group; E is selected from the group consisting of D-tryptophan or derivatives thereof, D-1-naphthylalanine, D-2-naphthylalanine, D-benzothienylalanine, D-4-bisphenylalanine and D-pentamethyl phenylalanine residues; the D-tryptophan derivative is selected from the group consisting of D-$N^{in}$-methyltryptophan, D-$N^{in}$-formyltryptophan and D-$N^{in}$-acetyltryptophan residues; More preferred ones are followings. A is a D-aspartic acid residue; X is a tryptophan, L-(β-4-phenylpiperazinamido)aspartic acid, L-[β-4-(2-methoxyphenyl)piperazinamid]aspartic acid, L-N(δ)-phenylacetylornithine (δ is a superscript, the same applies below), L-($N^4$-[indol-3-yl]acetyl)ornithine, L-(4-benzyloxy) proline, L-($N^5$-benzyl)glutamine or L-(N(δ)-[indol-3-yl] ethyl)asparagine residue; Y is an L-leucine, L-aspartic acid or L-O-benzylserine residue; B is a D-leucine, D-γ methyl leucine, D-2-thienylglycine or D-3-thienylglycine residue; C is selected from the group consisting of L-leucine, L-phenylalanine and L-tryptophan residues; and E is a D-tryptophan residue.

The anti-endothelin substance in the present invention is preferably the peptide(I) described in European Patent Publication No. 528312 and Japanese Patent Application No. 278722/1993.

Most preferably, the anti-endothelin substance is a peptide shown below.

(1) cyclo[—D—Asp—Asp(R1')—Asp—D—Thg(2)—Leu—D—Trp—], (2) cyclo[—D—Asp(OC$_2$H$_5$)—Asp(R1')—Asp(OC$_2$H$_5$)—D—Thg(2)—Leu—D—Trp—]

(3) cyclo[—D—Asp—Asp(B7)—Asp—DγMeLeu—Leu—D—Trp—]wherein Asp represents aspartic acid; Asp($R^{1'}$) represents aspartic acid β-4-phenylpiperazinamide; Thg (2) represents 2-thienylglycine; Leu represents leucine; Trp represents tryptophan; Asp(B7) represents aspartic acid β-4-(2-methoxyphenyl)piperazinamide; γMeLeu represents γ-methylleucine.

The above-described anti-endothelin substance, peptides in particular, may be used in the form of salts, preferably pharmacologically acceptable salts. Such salts may be organic or inorganic. Examples of the inorganic salts include salts with bases such as alkali metals (e.g., sodium and potassium), and polyvalent metals such as alkaline earth metals (e.g., calcium and magnesium), zinc, copper and aluminium and salts with inorganic acids (e.g., hydrochloric acid, hydrobromic acid, hydroiodic acid, sulfuric acid and phosphoric acid). Examples of organic salts include salts with organic acids such as carboxylic acid (e.g., formic acid, acetic acid, trifluoroacetic acid and maleic acid), organic sulfonic acid (methanesulfonic acid, benzenesulfonic acid and toluenesulfonic acid) and amino acids (e.g., arginine, aspartic acid and glutamic acid), ammonium salts and salts with organic bases such as tert-amine (e.g., trimethylamine, triethylamine, pyridine, picoline, dicyclohexylamine and N-N'-dibenzylethylenediamine). When the anti-endothelin substance has an acidic group such as carboxyl, sodium salts and salts with arginine are preferred. When the anti-endothelin substance has a basic group such as amino, hydrochlorides and acetates are preferred.

The above-described salts may be in the form of complexes. Examples of the complexes are complexes with alkali metals (e.g., sodium and potassium) and polyvalent metals such as alkaline earth metals (e.g., calcium and magnesium), zinc, copper and aluminium. The complexes are preferably complexes with polyvalent metals such as alkaline earth metals (e.g., calcium and magnesium), zinc, copper and aluminium, with greater preference given to a zinc complex.

The peptide represented by the general formula:

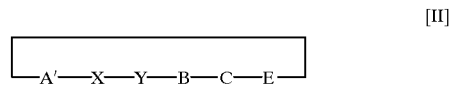

[II]

wherein A' represents a D-acidic-α-amino acid residue which is esterified with an alkyl group and other symbols have the same meanings as defined above, or a salt thereof, among the peptide [I], or ester thereof, or salt thereof, is novel.

In the D-acidic-α-amino acid residue which is esterified with an alkyl, represented by A', the alkyl group are exemplified by methyl, ethyl, n-propyl, iso-propyl, n-butyl, iso-butyl, tert-butyl, n-pentyl and n-hexyl, among which $C_{1-3}$ alkyl group such as methyl, ethyl, n-propyl and iso-propyl is preferred.

The peptide [II] or salt thereof is produced by subjecting the peptide [I] or salt thereof to a per se known esterification with an alkyl group.

When sustained-release preparations are produced by using the peptide [II] or salt thereof, thus obtained sustained-release preparations exhibit both suppression of initial burst of drug and constant release of drug.

The zinc salt of a peptide represented by the general formula [I] is novel.

The zinc salt of a peptide [I] is produced by mixing the peptide [I] or a water-soluble salt (e.g.: sodium salt) thereof with a water-soluble zinc salt in water. The zinc salt of peptide [I] precipitated is isolated by centrifugation and the like. Thus obtained precipitate is dispersed in distilled water and centrifuged again These operations are repeated to give a purified zinc salt of peptide [I]. The purified zinc salt of peptide [I] is subjected to drying such as vacuum drying and lyophilizing. The mixing ratio (peptide [I]/water-soluble zinc salt) (mol ratio) is about 10/1 to 1/10, preferably about 5/1 to 1/5. The concentration of these in water is within solubility of each and not lower than solubility of a produced complex. The above-mentioned water-soluble zinc salts are exemplified by inorganic acid zinc salts such as zinc halogenide (e.g., zinc chloride, zinc bromide, zinc iodide, zinc fluoride), zinc sulfate, zinc nitrate and zinc thiocyanate and organic acid zinc salts such as aliphatic carboxylic acid zinc salts (e.g., zinc acetate, zinc glycolate, zinc lactate, zinc tartrate) and aromatic acid zinc salts (e.g., zinc benzoate, zinc salicylate, zinc phenolsulfate). The water-soluble zinc salts are preferably aliphatic carboxylic acid zinc salts, with greater preference given to zinc acetate.

When sustained-release preparations are produced by using the zinc salt of the peptide [I], thus obtained sustained-release preparations exhibit both suppression of initial burst of drug and constant release of drug. The sustained-release preparations are high in drug content.

In the present invention, examples of means which can be used for sustained retention of the anti-endothelin substance in the living body are injectable sustained-release preparations (e.g., microcapsules and microspheres) using a biodegradable polymer, and indwellable preparations (shaped as needles, for example). Also available are electrically driven pumps or osmotic pressure pumps (Alzet etc.) capable of sustained release of a given amount of anti-endothelin substance. Other examples include preparations for non-invasive administration at such sites as the skin (percutaneous preparations), mucosa (transnasal preparations, transvaginal preparations etc.) and digestive tract (oral preparations, rectal suppositories etc.). The sustained-release preparation mentioned herein may be any preparation, as long as the pharmaceutical action is sustained for at least 24 hours after a single administration or an almost constant effective blood concentration lasts for at least 24 hours, with preference given to a preparation capable of sustaining the pharmaceutical action or an effective blood concentration for at least 72 hours after a single administration. Although an effective blood concentration may be sustained by increasing the frequency of administration in the case of oral preparations of short duration of action, increased frequency of administration is inconvenient for the patient and the degree of certainty is low. Microcapsular preparations using a biodegradable polymer are preferred because they are easy to administer and long in duration of action after administration. The anti-endothelin substance incorporated in the microcapsular preparation is preferably an endothelin antagonist. Although the amount of endothelin antagonist added varies depending on the activity thereof, target disease, duration of effect and other factors, the endothelin antagonist is used at normally about 0.001 to 50% (w/w), preferably about 0.01 to 30% (w/w), and more preferably about 0.1 to 20% (w/w), relative to the base biodegradable polymer.

Examples of biodegradable polymers include aliphatic polyesters (e.g., polymers, copolymers or mixtures thereof produced from one or more of α-hydroxycarboxylic acids such as glycolic acid, lactic acid and hydroxybutyric acid, hydroxydicarboxylic acids such as malic acid, hydroxytricarboxylic acids such as citric acid and others), poly-α-cyanoacrylic acid esters, polyamino acids (e.g., poly-γ-benzyl-L-glutamic acid) and maleic anhydride copolymers (e.g., styrene-maleic acid copolymers). These may be used as a mixture. Here, the type of polymerization may be random, block or graft.

The biodegradable polymer is preferably an aliphatic polyester (e.g., a polymer, copolymer or mixture thereof produced from one or more α-hydroxycarboxylic acids as glycolic acid, lactic acid and hydroxybutyric acid, hydroxydicarboxylic acids such as malic acid, hydroxytricarboxylic acids such as citric acid, and others).

Examples of the above-described copolymers include copolymers of glycolic acid and other α-hydroxy acids, the α-hydroxy acid being preferably lactic acid, 2-hydroxybutyric acid or the like. Although the α-hydroxycarboxylic acid may be a D-, L- or D,L-isomer, it is preferable that the ratio of the D-isomer/L-isomer (mol%) fall within the range from about 75/25 to 25/75. More preferably, the α-hydroxycarboxylic acid is a hydroxycarboxylic acid wherein the ratio of D-isomer/L-isomer (mol %) falls within the range from about 60/40 to 40/60.

With respect to the copolymer of glycolic acid and 2-hydroxybutyric acid, it is preferable that glycolic acid account for about 10 to 75 mol % and 2-hydroxybutyric acid account for the remaining portion. More preferably, glycolic acid accounts for about 20 to 75 mol %, still more preferably about 30 to 70 mol %. The glycolic acid copolymer has a weight-average molecular weight of about 2,000 to 50,000, preferably about 3,000 to 40,000, more preferably about 8,000 to 25,000. The dispersity of the glycolic acid copolymer (weight-average molecular weight/number-average molecular weight) is preferably about 1.2 to 4.0. Greater preference is given to a copolymer wherein the dispersity is about 1.5 to 3.5. The present glycolic acid copolymer can be produced by a known process such as the method described in Japanese Patent Unexamined Publication No. 28521/1986. It is preferable that the copolymer be produced by catalyst-free dehydration polymerization condensation.

The above-described glycolic acid copolymer may be used in a mixture with polylactic acid. Although the polylactic acid may be a D-isomer, L-isomer or a mixture thereof, it is preferable that the ratio of the D-isomer/L-isomer (mol %) fall within the range from about 75/25 to 20/80. More preferred is a polylactic acid wherein the ratio of the D-isomer/L-isomer (mol %) falls within the range from about 60/40 to 25/75, with greater preference given to a polylactic acid wherein the ratio of the D-isomer/L-isomer (mol %) falls within the range from about 55/45 to 25/75. The polylactic acid preferably has a weight-average molecular weight of about 1,500 to 30,000. More preferred is a polylactic acid wherein the weight-average molecular weight falls within the range from about 2,000 to 20,000, with greater preference given to a polylactic acid wherein the weight-average molecular weight falls within the range from about 3,000 to 15,000. Also, the dispersity of the polylactic acid is preferably about 1.2 to 4.0, more preferably about 1.5 to 3.5.

For producing polylactic acid, two methods are known: ring-opening polymerization of lactide, a dimer of lactic acid, and dehydration polymerization condensation of lactic acid. For obtaining a polylactic acid of relatively low molecular weight for the present invention, direct dehydration polymerization condensation of lactic acid is preferred. This method is, for example, described in Japanese Patent Unexamined Publication No. 28521/1986.

The present glycolic acid copolymer and polylactic acid are used over the mixing ratio range of, for example, from about 10/90 to 90/10 (% by weight), preferably from about 20/80 to 80/20, more preferably from about 30/70 to 70/30.

In the case of a copolymer of glycolic acid and lactic acid, the content ratio (lactic acid/glycolic acid) (mol %) is preferably about 100/0 to 40/60, more preferably about 90/10 to 45/55. The weight-average molecular weight of the copolymer of glycolic acid and lactic acid is preferably about 4,000 to 25,000, more preferably about 5,000 to 20,000.

The dispersity of the copolymer of glycolic acid and lactic acid (weight-average molecular weight/number average molecular weight) is preferably from about 1.2 to 4.0, more preferably from about 1.5 to 3.5. The copolymer of glycolic acid and lactic acid can be produced by a known method, such as the method described in Japanese Patent Unexamined Publication No. 2852111986. The copolymer is preferably produced by catalyst-free dehydration polymerization condensation.

In the present invention, the aliphatic polyester produced by catalyst-free dehydration polymerization condensation usually has a terminal carboxyl group.

More preferably, the biodegradable polymer is an aliphatic polyester (e.g., a polymer, copolymer or mixture thereof produced from one or more α-hydroxycarboxylic acids such as glycolic acid, lactic acid and hydroxybutyric acid, hydroxydicarboxylic acids such as malic acid, hydroxytricarboxylic acids such as citric acid, and others) as having a terminal carboxyl group.

A biodegradable polymer having a terminal carboxyl group is a polymer in which the number-average molecular weights by GPC determination and that by end-group determination almost agree.

To quantitate terminal free carboxyl groups, about 1 to 3 g of the biodegradable polymer is dissolved in a mixed solvent of acetone (25 ml) and methanol (5 ml), and the solution is quickly titrated with a 0.05N alcoholic solution of potassium hydroxide while stirring at room temperature with phenolphthalein as an indicator to determine the terminal carboxyl group content; the number-average molecular weight is calculated from the following equation:

Number-average molecular weight by end-group determination=20,000 A/B where A is the weight mass (g) of the biodegradable polymer, and B is the amount (ml) of the 0.05N alcoholic solution of potassium hydroxide added until the titration end point is reached.

This value is hereinafter referred to as number-average molecular weight by end-group determination.

For example, in the case of a polymer having a terminal carboxyl group, produced from one or more α-hydroxy acids by catalyst-free dehydration polymerization condensation, the number-average molecular weight by GPC determination and the number-average molecular weight by end-group determination almost agree with each other. On the other hand, in the case of a polymer having no terminal carboxyl groups and which is synthesized from a cyclic dimer by ring-opening polymerization using a catalyst, the number-average molecular weight by end-group determination is significantly higher than that by GPC determination. This difference makes it possible to clearly differentiate a polymer having a terminal carboxyl group from a polymer having no terminal carboxyl group.

While the number-average molecular weight by end-group determination is an absolute value, that by GPC determination is a relative value that varies depending on various analytical conditions (e.g., kind of mobile phase, kind of column, reference substance, slice width, baseline etc.); it is therefore difficult to have an absolute numerical representation of the latter. However, the description that the number-average molecular weights by GPC determination and end-group determination "almost agree" here denotes that the latter falls within the range from about 0.5 to 2 times, preferably from about 0.8 to 1.5 times, the former. Also, the description that the number-average molecular weight by end-group determination is "significantly higher" than the number-average molecular weight by GPC determination here denotes that the former is about 2 times or more greater than the latter.

In the present invention, preference is given to a polymer wherein the number-average molecular weights by GPC determination and by end-group determination almost agree.

Regarding weight-average molecular weights and number-average molecular weights by GPC determination, the present specification holds that the former is based on polystyrene obtained by gel permeation chromatography (GPC) with 9 polystyrenes as reference substances with weight-average molecular weights of 120,000, 52,000, 22,000, 9,200, 5,050, 2,950, 1,050, 580 and 162, respectively. Measurements were taken using a GPC column KF804Lx2 (produced by Showa Denko) and an RI monitor L-3300 (produced by Hitachi, Ltd.), with chloroform as a mobile phase.

The dispersity is calculated by the formula: (weight-average molecular weight/number-average molecular weight)

The sustained-release preparation of the present invention can, for example, be produced from a w/o emulsion with a solution containing an anti-endothelin substance as an internal aqueous phase and a solution containing a biodegradable polymer as an oil phase. This is achieved by known methods, including aqueous drying, phase separation, spray drying and modifications thereof.

The solvent used in the oil phase for the above-mentioned methods is preferably an organic solvent which dissolves biodegradable polymers and which has a boiling point not higher than 120° C. Such solvents include halogenated hydrocarbons (e.g., dichloromethane, chloroform and carbon tetrachloride), alcohols (e.g., ethanol and methanol) and acetonitrile. These may be used in combination. The solvent is preferably dichloromethane, acetonitrile or the like.

When the anti-endothelin substance for the present invention has a carboxyl group, its water solubility is low because it is often acidic; to increase its pharmaceutical solubility, it is often used in the form of an organic or inorganic salt. Such organic or inorganic salts are preferably alkali metal salts (e.g., sodium salt and potassium salt), with preference given to sodium salt. In order to include a pharmacologically necessary amount of drug, it is necessary to prepare a solution of very high concentration, however, since the volume of the aqueous phase for preparing the above w/o emulsion is usually very small. In such case, when the drug is low in water solubility, though soluble in water, it can fail to be completely dissolved, resulting in uneven mixing in preparing the emulsion. By dissolving the anti-endothelin substance along with an organic basic substance, a uniform solution of the anti-endothelin substance can be prepared that is soluble in water but low in solubility. Also, the addition of an organic basic substance suppresses the usually rapid initial drug release from microcapsules produced using a biodegradable polymer, allowing sustained release of a given amount of drug over a given period of time. The organic basic substance is preferably a basic amino acid, particularly arginine, histidine, lysine or the like. The organic basic substance is further exemplified by a peptide comprising two or more of basic amino acids such as arginyl-arginine.

As for the content ratio of the organic basic substance, the weight ratio of the anti-endothelin substance to the organic basic substance is normally 1:1,000 to 1,000:1, preferably 1:100 to 100:1, and more preferably 1:10 to 10:1. The weight ratio of the biodegradable polymer to the organic basic substance is normally 1,000:1 to 5:1, preferably 500:1 to 10:1, and more preferably 100:1 to 10:1.

In the process of producing sustained-release preparations, the addition of water-soluble polyvalent metal salts suppress the initial burst of drug, allowing sustained release of a given amount of drug over a given period of time and causing a high drug content. The water-soluble polyvalent metal salts may be any one, without limitation, as long as it is soluble in water and does not adversely affect the living body.

The water-soluble polyvalent metal salts are preferably polyvalent metal salts whose water solubility at normal temperature (about 20° C.) is over about 20 mg/ml, more preferably over about 100 mg/ml.

Examples of water-soluble polyvalent metal salts are polyvalent metal salts with inorganic acids and that with organic acids. Polyvalent metals are exemplified by alkaline earth metal (e.g., calcium, magnesium), zinc (II), iron (II, III), copper (II), tin (II, IV) and aluminium (II, III). Inorganic acids are exemplified by hydrohalogenic acid (e.g., hydrochloric acid, hydrobromic acid, hydroiodic acid, hydrofluoric acid), sulfuric acid, nitric acid and thiocyanic acid. Organic acids are exemplified by aliphatic carboxylic acid (e.g., acetic acid, glycolic acid, lactic acid, tartaric acid) and aromatic acid (e.g., benzoic acid, salycylic acid, phenolsulfonic acid). The water-soluble polyvalent metal salts are preferably water-soluble zinc salts. The water-soluble zinc salts are exemplified by inorganic acid zinc salts such as zinc halogenide (e.g., zinc chloride, zinc bromide, zinc iodide, zinc fluoride), zinc sulfate, zinc nitrate and zinc thiocyanate and organic acid zinc salts such as aliphatic carboxylic acid zinc salts (e.g., zinc acetate, zinc glycolate, zinc lactate, zinc tartrate) and aromatic acid zinc salts (e.g., zinc benzoate, zinc salicylate, zinc phenolsulfate). The water-soluble zinc salts are preferably aliphatic carboxylic acid zinc salts, with greater preference given to zinc acetate.

As for the content ratio of the water-soluble polyvalent metal salts, the weight ratio of the anti-endothelin substance to the water-soluble polyvalent metal salts is preferably 1:100 to 100:1, more preferably 1:10 to 10:1. The weight ratio of the biodegradable polymer to the water-soluble polyvalent metal salts is preferably 1,000:1 to 1:1, more preferably 100:1 to 2:1.

In the present invention, the anti-endothelin substance may be dissolved or suspended directly in an organic solvent solution of the biodegradable polymer. The anti-endothelin substance may be soluble or insoluble in the organic solvent. The anti-endothelin substance is sometimes soluble in the solution of the biodegradable polymer in the organic solvent, even when the anti-endothelin substance is insoluble in the organic solvent. Any organic solvent is acceptable, as long as it is substantially immiscible with water and dissolves the biodegradable polymer, and the resulting polymer solution dissolves the anti-endothelin substance. The organic solvent preferably has a water solubility not higher than 3% at normal temperature (20° C.). Also, the boiling point of the organic solvent is preferably not higher than 120° C. Example organic solvents include halogenated hydrocarbons (e.g., dichloromethane, chloroform, chloroethane, trichloroethane and carbon tetrachloride), ethers (e.g., isopropyl ether), fatty acid esters (e.g., butyl acetate) and aromatic hydrocarbons (e.g., benzene, toluene and xylene). These may be used in combination in appropriate ratios. The organic solvent is preferably dichloromethane. Dissolution of the anti-endothelin substance means that no anti-endothelin substance remains undissolved in the resulting solution, as examined by macroscopic observation at normal temperature (20° C.).

The sustained-release preparation of the present invention is preferably produced by, for example, the method of microcapsulation (or modification thereof) based on aqueous drying or phase separation as described below.

(i) Aqueous drying method (w/o/w method)

An anti-endothelin substance is dissolved in water. The anti-endothelin substance concentration in the aqueous solution is, for example, about 0.1 to 500% (w/v), preferably about 1 to 400% (w/v), and more preferably about 10 to 300% (w/v). To the aqueous solution, an organic basic substance, preferably a basic amino acid (e.g., arginine) or a peptide comprising two or more of basic amino acids (e.g., arginyl-arginine) may be added. The concentration of the organic basic substance used for this purpose in the aqueous solution is about 0.01 to 500% (w/v), preferably about 0.1 to 400% (w/v), and more preferably about 1 to 300% (w/v). To the aqueous solution, water-soluble polyvalent metals may be added in the same manner as the organic basic substance. To the aqueous solution may be added pH regulators (e.g., acetic acid, hydrochloric acid and sodium hydroxide), stabilizers (e.g., serum albumin and gelatin), preservatives (paraoxybenzoic acids) and other additives. The aqueous solution thus obtained is emulsified and dispersed in an organic solvent solution of a biodegradable polymer or copolymer synthesized from α-hydroxycarboxylic acid to yield a w/o emulsion. Although the biodegradable polymer concentration in the organic solvent solution varies depending on the molecular weight of the biodegradable polymer and the kind of organic solvent, it is selected over the range from about 0.01 to 80% (w/w), preferably about 0.1 to 70% (w/w), and more preferably about 1 to 60% (w/w).

The ratio of the aqueous solution and the organic solvent solution of the biodegradable polymer is normally 1:1,000 (v/v) to 1:1 (v/v), preferably 1:100 (v/v) to 1:5 (v/v), and more preferably 1:50 (v/v) to 1:5 (v/v). This emulsification is achieved by known methods of dispersion using a turbine type mechanical stirrer, homogenizer etc.

The w/o emulsion thus prepared is added to an aqueous phase to form a w/o/w emulsion, followed by evaporation of the solvent in the oil phase, to yield microcapsules. The volume of the aqueous phase is chosen over the range normally from about 1 to 10,000 times, preferably from about 2 to 5,000 times, and more preferably from about 5 to 2,000 times the volume of the oil phase.

In addition to the above additives, an emulsifier may be added to the aqueous phase. The emulsifier may be any one, as long as it is capable of forming a stable o/w emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin and hyaluronic acid. These may be used singly or in combination. The concentration of emulsifier used may be chosen as appropriate over the range normally from about 0.001 to 20% (w/w), preferably from about 0.01 to 10% (w/w), and more preferably from about 0.05 to 5% (w/w).

The microcapsules thus obtained are collected by centrifugation or filtration, after which they are repeatedly washed with distilled water in several cycles to remove the free anti-endothelin substance, emulsifier etc. adhering to the microcapsule surface, again dispersed in distilled water etc. and then lyophilized. Where necessary, the microcapsules are heated under reduced pressure to further remove the water and organic solvent. Preferably, this removal is carried out at a heating rate of 10 to 20° C. per minute at a temperature higher by at least 5° C. than the intermediate glass transition point of the biodegradable polymer, as determined using a differential scanning calorimeter, usually within 1 weeks or 2 or 3 days, more preferably within 24 hours, after the microcapsules have reached a given temperature.

(ii) Aqueous drying method (o/w method)

An anti-endothelin substance is added to an organic solvent solution of a biodegradable polymer to a ratio by weight as defined above, to prepare an organic solvent solution or suspension containing both the anti-endothelin substance and the biodegradable polymer. In this operation, the biodegradable polymer concentration in the organic solvent solution varies depending on the molecular weight of the biodegradable polymer and the kind of the organic solvent, it is chosen over the range normally from about 0.01 to 80% (w/w), preferably from about 0.1 to 70% (w/w), and more preferably from about 1 to 60% (w/w). To the organic solvent solution or suspension, water-soluble polyvalent salts may added.

The organic solvent solution or suspension thus prepared is added to an aqueous phase to form an o/w emulsion, followed by evaporation of the solvent in the oil phase, to yield microcapsules. The volume of the aqueous phase is chosen over the range normally from about 1 to 10,000 times, preferably from about 2 to 5,000 times, and more preferably from about 5 to 2,000 times the volume of the oil phase.

In addition to the above additives, an emulsifier may be added to the aqueous phase. The emulsifier may be any one, as long as it is capable of forming a stable o/w emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin and hyaluronic acid. These may be used singly or in combination. The concentration of the emulsifier used may be chosen as appropriate over the range normally from about 0.001 to 20% (w/w), preferably from about 0.01 to 10% (w/w), and more preferably from about 0.05 to 5% (w/w).

The microcapsules thus obtained are collected by centrifugation or filtration, after which they are repeatedly washed with distilled water in several cycles to remove the free anti-endothelin substance, emulsifier etc. adhering to the microcapsule surface, and again dispersed in distilled water etc. and then lyophilized. Where necessary, the microcapsules are then heated under reduced pressure to further remove water and organic solvent. Preferably, this removal is achieved at a heating rate of 10 to 20° C. per minute at a temperature higher by at least 5° C. than the intermediate glass transition point of the biodegradable polymer, as determined using a differential scanning calorimeter, usually within 1 weeks or 2 or 3 days, more preferably within 24 hours after the microcapsules have reached a given temperature.

(iii) Phase separation method

In producing microcapsules by the phase separation method, a coacervating agent is gradually added to the above-described w/o emulsion or organic solvent solution during stirring, to separate and solidify the biodegradable polymer. The coacervating agent is added in an amount by volume about 0.01 to 1,000 times, preferably about 0.05 to 500 times, and more preferably about 0.1 to 200 times the volume of the w/o emulsion or organic solvent solution.

Any coacervating agent is acceptable, as long as it is a polymer, mineral oil or vegetable oil compound that is miscible in the solvent for the biodegradable polymer and which does not dissolve the polymer. Example coacervating agents include silicon oil, sesame oil, soybean oil, corn oil, cotton seed oil, coconut oil, linseed oil, mineral oil, n-hexane and n-heptane. These may be used in combination.

The microcapsules thus obtained are collected by filtration, after which they are repeatedly washed with heptane etc. to remove the coacervating agent. The free drug and solvent are removed in the same manner as in the aqueous drying method.

Solvent removal can be achieved by known methods, including the method in which the solvent is evaporated under normal or gradually reduced pressure during stirring using a propeller stirrer or magnetic stirrer, and the method in which the solvent is evaporated while adjusting the degree of vacuum using a rotary evaporator etc.

In production by the aqueous drying method or coacervation method, an antiflocculant may be added to prevent grain flocculation. The antiflocculant is exemplified by water-soluble polysaccharides such as mannitol, lactose, glucose and starches (e.g., corn starch), proteins such as glycine, fibrin and collagen and inorganic salts such as sodium chloride and sodium hydrogen phosphate.

In producing microcapsules by the spray drying method, a w/o emulsion or organic solvent solution containing the above-described anti-endothelin substance and biodegradable polymer is sprayed via a nozzle into the drying chamber of a spray drier to volatilize the organic solvent in the fine droplets in a very short time to yield fine microcapsules. The nozzle is exemplified by the double-fluid nozzle, pressure nozzle and rotary disc nozzle. Where desired, to prevent microcapsule flocculation, an aqueous solution of the above-described antiflocculant may be effectively sprayed via another nozzle simultaneously with spraying of the w/o emulsion or organic solvent solution containing the anti-endothelin substance and biodegradable polymer.

The microcapsules thus obtained may have their water and organic solvent removed at increased temperature under reduced pressure as necessary.

The above-described microcapsules can be administered as such or in the form of various dosage forms of non-oral preparations (e.g., intramuscular, subcutaneous or visceral injections or indwellable preparations, nasal, rectal or uterine transmucosal preparations) or oral preparations (e.g., capsules such as hard capsules and soft capsules), or solid preparations such as granules and powders or liquid preparations such as syrups, emulsions and suspensions.

In addition to the above-described dosage forms of microcapsules, the w/o emulsion or organic solvent solution containing an anti-endothelin substance and biodegradable polymer can be shaped in rods, needles, pellets, films and other forms and administered as intramuscular, subcutaneous or visceral injections or indwellable preparations, nasal, rectal or uterine transmucosal preparations, oral preparations (e.g., capsules such as hard capsules and soft capsules), solid preparations such as granules and powders, and liquid preparations such as syrups, emulsions and suspensions.

The injectable preparation of the present invention can be produced by known methods. The injectable preparation is produced by, for example, suspending the above-described sustained-release preparation of microcapsules etc. in water, along with a dispersing agent (e.g., surfactants such as Tween 80 and HCO-60, and polysaccharides such as carboxymethyl cellulose and sodium alginate), a preservative (e.g., methyl paraben and propyl paraben), an isotonizing agent (e.g., sodium chloride, mannitol, sorbitol and glucose), to yield an aqueous suspension, or by dispersion in a vegetable oil such as sesame oil or corn oil or middle-chain fatty acid triglyceride (e.g., Migriol 812) to yield an oily suspension. The particle size of the sustained-release preparation is chosen over the range from about 0.1 to 300 μm, for instance, as long as the requirements concerning the degree of dispersion and needle passage are met, when the sustained-release preparation is used as an injectable suspension. Preferably, the particle size falls within the range from about 1 to 150 μm, more preferably from about 2 to 100 μm. A sustained-release preparation can be prepared as a sterile preparation without limitation by the method in which the entire production process is sterile, the method in which a gamma ray is used as a sterilant, and the method in which an antiseptic is added.

With low toxicity, the sustained-release preparation of the present invention can be safely used in mammals (e.g., humans, bovines, swines, dogs, cats, mice, rats and rabbits).

The sustained-release preparation of the present invention is used to treat or prevent endothelin-associated diseases, particularly chronic ones. Such diseases include cardiac/cerebral circulatory diseases, renal diseases, hypertension (e.g., pulmonary hypertension), asthma, inflammation, arthritis, hepatic cancer, cirrhosis and chronic complications in diabetes mellitus. The sustained-release preparation of the present invention is used to treat or prevent arteriosclerosis, diabetic nephropathy, diabetic myocarditis and diabetic retinopathy, in particular.

Varying depending on type, content and dosage form of the active ingredient anti-endothelin substance, duration of anti-endothelin substance release, target disease (e.g., diabetic nephropathy), subject animal and other factors, the dose of the sustained-release preparation may be set at levels such that the anti-endothelin substance is effective. The dose per administration of the active ingredient anti-endothelin substance is chosen as appropriate over the range from about 0.01 to 100 mg/kg body weight for each adult when the preparation is a 1-month preparation. More preferably, the dose may be chosen as appropriate over the range from about 0.05 to 50 mg/kg body weight.

The dose per administration of the sustained-release preparation is chosen as appropriate over the range from about 0.1 to 1,000 mg/kg body weight for each adult. More preferably, the dose may be chosen as appropriate over the range from about 0.5 to 500 mg/kg body weight. Dosing frequency can be chosen as appropriate, e.g., once weekly, once every several weeks, once monthly or once every several months, depending on type, content and dosage form of the active ingredient anti-endothelin substance, duration of anti-endothelin substance release, subject disease, subject animal and other factors.

The preparation of the present invention may be used in combination with other drugs, specifically conventional therapeutic drugs for diabetic nephropathy, such as hypotensive drugs. Although the preparation of the present invention may be stored at normal temperatures or cold places, it is preferable to store it at a cold place. Normal temperatures and cold places mentioned herein are as defined by the Pharmacopoeia of Japan.

The present invention is hereinafter described in more detail by means of the following working examples and experimental examples, which are not to be construed as limitative.

REFERENCE EXAMPLE 1

Synthesis of cyclo[—D—Asp—Asp(B7)—Asp—D—γMeLeu—Leu—D—Trp—]disodium salt 4.4 g of cyclo(—D—Asp—Asp(B7)—Asp—D—γMeLeu—Leu—D—Trp—] (hereinafter referred to briefly as peptide B) was dissolved in 50 ml of methanol and concentrated. The concentrate was again dissolved in 50 ml of methanol and subjected to ice cooling. To thus obtained solution 0.1N NaOH solution (46.4 ml) was added dropwise, and the pH of the solution was adjusted to 7–8 by further addition of 0.1N NaOH solution. The resulting solution was concentrated. The concentrate was lyophilized after addition of distilled water. Peptide B disodium salt (Yield 4.5 g)

Elemental analysis: As $C_{47}H_{61}N_9O_{11}Na2.CF_3CO_2Na.0.5CH_3CO_2Na.3H_2O$ Calculated: C, 49.18; H, 5.65; N, 10.32 Found: C, 49.08; H, 5.50; N, 10.33

EXAMPLE 1

51 mg of the disodium salt of the cyclic peptide cyclo (—D—Asp—Asp(R1')—Asp—D—Thg(2)—Leu—D—Trp—]wherein Asp represents aspartic acid; Asp(R1') represents aspartic acid β-4-phenylpiperazinamide; Thg(2) represents 2-thienylglycine; Leu represents leucine; Trp represents tryptophan, described in European Patent Publication No. 528312 and 49 mg of L-arginine (Wako Pure Chemical) were dissolved in 300 ul of distilled water. This solution was added to a solution of 1.92 g of a lactic acid-glycolic acid copolymer (lactic acid/glycolic acid=75/25 mol %, GPC weight-average molecular weight 14,000, GPC number-average molecular weight 2,000, number-average molecular weight by end-group determination 2,200, produced by Wako Pure Chemical Industry, Lot No. 920729) in 2 ml of dichloromethane, and the mixture was stirred using a homogenizer (Polytron) to yield a w/o emulsion. After cooling to 17° C., the emulsion was injected to 1,000 ml of a 0.1% (w/w) aqueous solution of polyvinyl alcohol (EG-40, produced by The Nippon Synthetic Chemical Industry, Co., Ltd.), previously adjusted to 16° C., followed by stirring in a turbine homomixer at 7,000 rpm to yield a w/o/w emulsion, which was then stirred at room temperature for 3 hours to volatilize the dichloromethane and solidify the oil phase, which was then collected via centrifugation at 2,000 rpm using a centrifuge (05PR-22, Hitachi, Ltd.). The precipitate was again dispersed in distilled water, centrifuged and washed to remove the free drug etc. After the collected microcapsules were re-dispersed in a small amount of distilled water, 0.3 g of D-mannitol was added, and the dispersion was lyophilized to yield powdery microcapsules.

EXAMPLE 2

About 39 mg of microcapsules as obtained in Example 1 was dispersed in 1.95 ml of a dispersant for injection (distilled water containing 2.5 mg of carboxymethyl cellulose, 0.5 mg of polysorbate 80 and 25 mg of mannitol, all dissolved therein) to yield an injectable preparation.

EXAMPLE 3

3.6 g of lactic acid-glycolic acid copolymer (lactic acid/glycolic acid=75/25 mol %, GPC weight-average molecular weight 15,038, GPC number-average molecular weight 5,195, produced by Wako Pure Chemical Industry) was dissolved in 6.6 g (5 ml) of dichloromethane. To this solution was added a solution of peptide A disodium salt (250 mg) and L-arginine (100 mg) in 0.5 ml of distilled water, and the mixture was stirred for about 30 seconds using a homogenizer (Polytron) to yield a w/o emulsion. The emulsion was injected to 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a w/o/w emulsion, which was then stirred at a room temperature for 3 hours to volatile the dichloromethane and solidify the oil phase, which was then collected via centrifugation at 2,000 rpm using a centrifuge (05PR-22, Hitachi, Ltd.). The precipitate was again dispersed in distilled water, centrifuged and washed to remove the free drug etc. After 100 mg of D-mannitol was added to the collected microcapsules, the microcapsules were re-dispersed in a small amount of distilled water, and the dispersion was lyophilized to yield powdery microcapsules.

The microcapsules thus obtained were homogenized and extracted in 0.1M ammonium acetate solution containing 30% (v/v) acetonitrile for 3 hours, and then assayed by HPLC (high performance liquid chromatography).

As the result, the content of peptide A disodium salt was 5.2 mg per 100 mg of microcapsules.

EXAMPLE 4

Powdery microcapsules were obtained in the same manner as Example 3, except that L-arginyl-arginine (Kokusan Chemical Works Ltd.) was substituted for L-arginine.

The content of peptide A disodium salt was 7.4 mg per 100 mg of microcapsules.

EXAMPLE 5

Synthesis of cyclo[—D—Asp($OC_2H_5$)—Asp(R1')—Asp($OC_2H_5$)—D—Thg(2)—Leu—D—Trp—]

10 ml of ethanol was cooled to $-10°$ C. in a dry ice-acetone bath, and 2.6 ml of thionyl chloride was added in a small amount. After 5 minutes, 1.0 g of peptide A disodium salt was added to the mixture and stirred at room temperature. After 2 hours, ethanol and excess thionyl chloride was removed under reduced pressure to give an oily substance. The oily substance was dissolved in a small amount of ethanol, and again the solvent was removed under reduced pressure. This operation was repeated three times and a small amount of diethylether was added to give 1.05 g of titled compound. The result of analysis of peptide A diethylester was described below.

1) Mass spectrometry (LSIMS method):

$[M+H]^+$=984 (theoretical value=984)

$[M+Na]^+$=1,006 (theoretical value=1,006)

2) Elemental analysis: As $C_{49}H_{61}N^9O_{11}S \cdot 2NaCl \cdot 2H_2O \cdot HCl$ Calculated: C, 50.20; H, 5.67; N, 10.75 Found: C, 50.35; H, 5.75; N, 10.81

EXAMPLE 6

0.5 g of lactic acid-glycolic acid copolymer (lactic acid/glycolic acid=50/50 ml %, GPC weight-average molecular weight 5,900, GPC number-average molecular weight 2,600, produced by Wako Pure Chemical Industry) was dissolved in 6.6 g (5 ml) of dichloromethane. To this solution was added 0.15 g of peptide A diethylester which was obtained in Example 5, and the mixture was stirred for about 30 seconds using a homogenizer (Polytron) to yield a s/o emulsion. The emulsion was injected to 400 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a s/o/w emulsion, which was then stirred at a room temperature for 3 hours to volatile the dichloromethane and solidify the oil phase, which was then collected via centrifugation at 2,000 rpm using a centrifuge (05PR-22, Hitachi, Ltd.). The precipitate was again dispersed in distilled water, centrifuged and washed to remove the free drug etc. After 50 mg of D-mannitol was added to the collected microcapsules, the microcapsules were re-dispersed in a small amount of distilled water, and the dispersion was lyophilized to yield powdery microcapsules.

The microcapsules thus obtained were homogenized and extracted in 0.1M phosphate buffered solution containing 50% acetinitrile for 3 hours, and then assayed by HPLC (high performance liquid chromatography).

As the result, the content of peptide A diethylester was 25.2 mg per 100 mg of microcapsules.

EXAMPLE 7

3.2 g of peptide A disodium salt and 7.28 g of zinc acetate di-hydrate were each dissolved in 160 ml of distilled water, and thus obtained two solutions were mixed together. This mixture was stayed at 4° C. for a day, and then centrifuged at 3,000 rpm using a centrifuge (05PR-22, Hitachi, Ltd.). Thus obtained precipitate was again dispersed in distilled water, centrifuged and washed to remove the free drug etc. After small amount of distilled water was added to the collected precipitate to re-disperse the precipitate, the dispersion was lyophilized to yield a crude peptide A zinc salt as a 2.81 g of dried powder.

The dried powder thus obtained were homogenized and extracted in 50 mM EDTA solution containing 30% (v/v) acetonitrile for 3 hours, and then assayed by HPLC (high performance liquid chromatography).

As the result, the content of peptide A in dried powder was 80.7% (w/w).

EXAMPLE 8

0.97 g of lactic acid-glycolic acid copolymer (lactic acid/glycolic acid=75/25 mol %, GPC weight-average molecular weight 15,038, GPC number-average molecuar weight 5,195, produced by Wako Pure Chemical Industry) was dissolved in 13.2 g (10 ml) of dichloromethane. To this solution was added the crude peptide A zinc salt (300 mg) which was obtained in Example 7, and the mixture was stirred for about 30 seconds using a homogenizer (Polytron) to yield a s/o emulsion. The emulsion was injected to 400 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a s/o/w emulsion, which was then stirred at a room temperature for 3 hours to volatile the dichloromethane and solidify the oil phase, which was then collected via centrifugation at 2,000 rpm using a centrifuge (05PR-22, Hitachi, Ltd.). The precipitate was again dispersed in distilled water, centrifuged and washed to remove the free drug etc. After 50 mg of D-mannitol was added to the collected microcapsules, the microcapsules were re-dispersed in a small amount of distilled water, and the dispersion was lyophilized to yield powdery microcapsules.

The microcapsules thus obtained were homogenized and extracted in 50 mM EDTA (ethylenediaminetetraacetic acid) solution containing 30% (v/v) acetonitrile for 3 hours, and then assayed by HPLC (high performance liquid chromatography).

As the result, the content of a crude peptide A zinc salt in terms of peptide A disodium salt was 21.2 mg per 100 mg of microcapsules.

EXAMPLE 9

Powdery microcapsules were obtained in the same manner as Example 3, except that peptide B disodium salt was substituted for peptide A disodium salt.

The content of peptide B disodium salt was 5.2 mg per 100 mg of microcapsules.

EXAMPLE 10

1.2 g of lactic acid-glycolic acid copolymer (lactic acid/glycolic acid=75/25 mol %, GPC weight-average molecular weight 13,585, GPC number-average molecular weight 4,413, produced by Wako Pure Chemical Industry) was dissolved in 26.4 g (20 ml) of dichloromethane. To this solution was added a solution of peptide A disodium salt (400 mg) and zinc acetate di-hydrate (400 mg) in 1.7 ml of distilled water, and the mixture was stirred for about 30 seconds using a homogenizer (Polytron) to yield a w/o emulsion. The emulsion was injected to 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a w/o/w emulsion, which was then stirred at a room temperature for 3 hours to volatile the dichloromethane and solidify the oil phase, which was then collected via centrifugation at 2,000 rpm using a centrifuge (05PR-22, Hitachi, Ltd.). The precipitate was again dispersed in distilled water, centrifuged and washed to remove the free drug etc. After 50 mg of D-mannitol was added to the collected microcapsules, the microcapsules were re-dispersed in a small amount of distilled water, and the dispersion was lyophilized to yield powdery microcapsules.

The microcapsules thus obtained were homogenized and extracted in 50 mM EDTA solution containing 30% (v/v) acetonitrile for 3 hours, and then assayed by HPLC (high performance liquid chromatography).

As the result, the content of peptide A disodium salt was 12 mg per 100 mg of microcapsules.

EXAMPLE 11

1.4 g of lactic acid-glycolic acid copolymer (lactic acid/glycolic acid=75/25 mol %, GPC weight-average molecular weight 13,585, GPC number-average molecular weight 4,413, produced by Wako Pure Chemical Industry) was dissolved in 6.6 g (5 ml) of dichloromethane. To this solution was added peptide A disodium salt (437 mg) and zinc acetate di-hydrate (467 mg), and the mixture was stirred for about 30 seconds using a homogenizer (Polytron) to yield a s/o emulsion. The emulsion was injected to 800 ml of a 0.1% (w/w) aqueous solution of polyvinyl alcohol (EG-40, produced by The Nippon Synthetic Chemical Industry, Co., Ltd.), previously adjusted to 18° C., followed by stirring in a turbine homomixer at 6,000 rpm to yield a s/o/w emulsion, which was then stirred at a room temperature for 3 hours to volatile the dichloromethane and solidify the oil phase, which was then collected via centrifugation at 2,000 rpm using a centrifuge (05PR-22, Hitachi, Ltd.). The precipitate was again dispersed in distilled water, centrifuged and washed to remove the free drug etc. After 50 mg of D-mannitol was added to the collected microcapsules, the microcapsules were re-dispersed in a small amount of distilled water, and the dispersion was lyophilized to yield powdery micro capsules.

The microcapsules thus obtained were homogenized and extracted in 50 mM EDTA solution containing 30% (v/v) acetonitrile for 3 hours, and then assayed by HPLC (high performance liquid chromatography).

As the result, the content of peptide A disodium salt was 12.2 mg per 100 mg of microcapsules.

COMPARATIVE EXAMPLE 1

Powdery microcapsules were obtained in the same manner as Example 3, except that peptide A disodium salt was not used.

COMPARATIVE EXAMPLE 2

1.6 g of peptide A disodium salt and 3.65 g of zinc acetate were each dissolved in 80 ml of distilled water, and thus obtained two solutions were mixed together. This mixture was centrifuged at 3,000 rpm using a centrifuge (05PR-22, Hitachi, Ltd.). Thus obtained precipitate was again dispersed in distilled water, centrifuged and washed to remove the free drug etc. After a small amount of distilled water was added to the collected precipitate to re-disperse the precipitate, the dispersion was lyophilized to yield a crude peptide A zinc salt as 1.23 g of a dried powder.

EXPERIMENTAL EXAMPLE 1

An injectable preparation as obtained in Example 2 was subcutaneously administered to the back of 8-week-old male SD rats. After administration, rats were killed at given intervals and the microcapsules remaining at the administration site were taken out and assayed for drug content. This procedure was repeated to obtain the time course of drug release from the microcapsules given to the live body. The results are shown in FIG. 1. The drug content in the microcapsules given to the live body decreased over a period of 1 month or more, demonstrating that the anti-endothelin substance could be sustained in the live body.

EXPERIMENTAL EXAMPLE 2

About 100 mg of microcapsules as obtained in Example 1 were dispersed in 2.5 ml of a dispersant for injection (distilled water containing 2.5 mg of carboxymethyl cellulose, 0.5 mg of polysorbate 80 and 25 mg of mannitol, all dissolved therein). The resulting dispersion was subcutaneously administered to the back of 13-week-old male Wistar fatty rats. The male Wistar fatty rat, a line of rat which genetically develops obesity and hyperglycemia, is characterized by increased leakage of protein and albumin in urine with the development of hyperglycemia. The results of urinary protein and albumin assays in a control group receiving no microcapsules and an administration group receiving the microcapsule are given in Table 1.

TABLE 1

| Weeks after administration | 0 | 2 | 4 | 6 | 8 |
|---|---|---|---|---|---|
| Urinary Albumin (mg/day, mean) | | | | | |
| Control group | 9 | — | 32 | — | 37 |
| Administration group | 6 | — | 18 | — | 23 |
| Urinary Protein (mg/day, mean) | | | | | |
| Control group | 97 | 98 | 83 | 112 | 132 |
| Administration group | 98 | 68 | 68 | 64 | 92 |

As seen in Table 1, during the period of about 6 weeks after microcapsule administration, smaller amounts of protein and albumin were excreted in the urine, in comparison with the initial values and control values. These results demonstrate that urinary protein and albumin excretion, a symptom of diabetic nephropathy, were suppressed during the period when the endothelin antagonist was sustained in the live body as shown in Experimental Example 1, suggesting the utility of the present invention as a therapy for diabetic nephropathy.

EXPERIMENTAL EXAMPLE 3

About 190 mg of microcapsules as obtained in Example 3 were dispersed in 1.5 ml of dispersant for injection (distilled water containing 7.5 mg of carboxymethyl cellulose, 1.5 mg of polysorbate 80 and 75 mg of mannitol, all dissolved therein). The resulting dispersion was subcutaneously administered to the back of 8-week-old male Wistar fatty rats using 18 G needles (the dosage of peptide A disodium salt per one rat was about 10 mg). The same administration was conducted once a month for 3 months. As a control, microcapsules containing no peptide A disodium salt as obtained in Comparative Example 1 were subcutaneously administered to the back of 8-week-old male Wistar fatty rats.

At regular intervals after administration, excreted urine was sampled and urinary albumin was assayed. As seen in Table 2, 9 and 12 weeks after the administration, the urinary albumin excretion in an administration group receiving the microcapsules of Example 2 was suppressed, compared with that in a control group.

TABLE 2

| | Urinary Albumin (mg/day, mean) | | |
|---|---|---|---|
| Weeks after administration | 0 | 9 | 12 |
| Control group | 2 ± 1 | 32 ± 8 | 45 ± 10 |
| Administration group | 3 ± 1 | 17 ± 4 | 26 ± 11 |

EXPERIMENTAL EXAMPLE 4

6-week-old male Wistar rats anaesthetized with pentobarbital were innoculated with 25 mg of deoxycorticosterone after surgical removal of left-hand side kidney. The rats were allowed to drink 1% (w/v) of saline solution freely for 3 weeks. The microcapsules as obtained in Example 3 were dispersed in a dispersant for injection (2.5 mg of carboxymethyl cellulose, 0.5 mg of polysorbate 80 and 25 mg of mannitol, all dissolved in 0.5 ml of distilled water) to get 100 mg/ml of peptide A disodium salt in the resulting dispersion. The dispersion was subcutaneously administered to the back of the rats using 18 G needles (the dosage of peptide A disodium salt was 100 mg/kg). As a control, microcapsules containing no peptide A disodium salt as obtained in Comparative Example 1 were subcutaneously administered to the back of 6-week-old male Wistar rats which were treated in the same manner.

As the results, systolic pressure in an administration group receiving the microcapsules of Example 3 began to decrease at one week after administration, and was kept lower by about 28 and 25 mmHg compared with that in a control group each until 2 and 4 weeks after administration. These results demonstrate that the sustained release of anti-endothelin substance makes it possible to keep blood pressure low.

EXPERIMENTAL EXAMPLE 5

5-week-old male Wistar rats surgically innoculated with Mini Osmotic Pump (Alzet Model 2002, produced by Alza) containing 45 mg of peptide A disodium salt were subcutaneously administered with monocrotaline (100 mg/kg). The Mini Osmotic Pump were replaced after 2 weeks. The release rate of peptide A disodium salt from the Mini Osmotic Pump was 2.5 mg/rat/day, calculated from the remaining amount of peptide A disodium salt in the removed Mini Osmotic Pump. As a control, Mini Osmotic Pump containing no peptide A disodium salt were surgically innoculated in 5-week-old male Wistar rats, and the rats were treated in the same manner. At 4 weeks after monocrotaline administration, chests of the rats anaesthetized with pentobarbital were surgically opened under artificial respiration, and the pressure of right ventricles was monitored via an inserted catheter after a steady stae was achieved.

As the results, in the group treated with peptide A disodium salt, elevation of right ventricle pressure was moderately suppressed (lower by 26 mmHg compared with a control group). In addition, hypertrophy of right ventricle was not significant (lower by 0.23 mg tissue/g body weight) compared with the control group. These results demonstrate that the sustained presence of endothelin antagonist in blood is effective enough to improve the pathology of pulmonary hypertension, and that sustained release preparation of anti-endothelin substance is useful in the treatment of pulmonary hypertension.

EXPERIMENTAL EXAMPLE 6

About 30 mg of the microcapsules as obtained in Example 6 were dispersed in 0.5 ml of a dispersant for injection (distilled water containing 2.5 mg of carboxymethyl cellulose, 0.5 mg of polysorbate 80 and 25 mg of mannitol, all dissolved therein). The resulting dispersion was subcutaneously administered to the back of 9-week-old SD rats using 20 G needles (the dosage of peptide A diethylester per one rat was about 12.6 mg). At regular intervals after administration, blood was gathered from rats tails and the concentration of peptide A diethylester in serum was assayed by EIA (Enzyme immunoassay). As seen in Table 3 almost constant blood concentration was kept for 2 weeks.

TABLE 3

| peptide A diethylester in serum (ng/ml) | | | |
|---|---|---|---|
| Days after administration | 1 | 7 | 4 |
| Administration group | 17.8 | 19.7 | 12.5 |

EXPERIMENTAL EXAMPLE 7

About 50 mg of the microcapsules as obtained in Example 8 were dispersed in 0.5 ml of a dispersant for injection (distilled water containing 2.5 mg of carboxymethyl cellulose, 0.5 mg of polysorbate 80 and 25 mg of mannitol, all dissolved therein). The resulting dispersion was subcutaneously administered to the back of 6-week-old SD rats using 20 G needle s (the dosage of a crude peptide A zinc salt per one rat was about 10 mg in terms of peptide A disodium salt). At regular intervals after administration, blood was gathered from rats tails and the concentration of peptide A in serum was assayed by EIA. The results are given in Table 4. The amount of a peptide A zinc salt in the table is calculated in terms of peptide A disodium salt.

TABLE 4

| peptide A zinc salt in serum (ng/ml) | | | | |
|---|---|---|---|---|
| Days after administration | 1 | 7 | 14 | 21 |
| Administration group | 5.09 | 6.50 | 10.18 | 11.23 |

As seen in Table 4, an almost constant blood concentration was kept for 3 weeks in an administration group receiving the preparation of Example 7. As a control, a crude peptide A zinc salt as obtained in Comparative Example 2 was dispersed in the dispersant for injection and was subcutaneously administered to rats (the dosage of a crude peptide A zinc salt per one rat was about 10 mg in terms of peptide A disodium salt), then peptide A in serum was decreased to be undetectable 3 days after the administration.

EXPERIMENTAL EXAMPLE 8

About 70 mg of the microcapsules as obtained in Example 10 were dispersed in 0.5 ml of a dispersant for injection (distilled water containing 2.5 mg of carboxymethyl cellulose, 0.5 mg of polysorbate 80 and 25 mg of mannitol, all dissolved therein). The resulting dispersion was subcutaneously administered to the back of 6-week-old SD rats using 20 G needles (the dosage of peptide A disodium salt per one rat was about 10 mg). At regular intervals after administration, blood was gathered from rats tails and the concentration of peptide A disodium salt in serum was assayed by EIA. The results are given in Table 5.

TABLE 5

| peptide A disodium salt in serum (ng/ml) | | | | |
|---|---|---|---|---|
| Days after administration | 1 | 7 | 14 | 21 |
| Administration group | 11.12 | 26.77 | 8.37 | 5.74 |

As seen in Table 5, an almost constant blood concentration was kept for 2 weeks in an administration group receiving the preparation of Example 10.

EXPERIMENTAL EXAMPLE 9

About 70 mg of the microcapsules as obtained in Example 11 were dispersed in 0.5 ml of a dispersant for injection (distilled water containing 2.5 mg of carboxymethyl cellulose, 0.5 mg of polysorbate 80 and 25 mg of mannitol, all dissolved therein). The resulting dispersion was subcutaneously administered to the back of 6-week-old SD rats using 20 G needles (the dosage of peptide A disodium salt per one rat was about 10 mg). At regular intervals after administration, blood was gathered from rats tails and the concentration of peptide A disodium salt in serum was assayed by EIA. The results are given in Table 6.

TABLE 6

| peptide A disodium salt in serum (ng/ml) | | | |
|---|---|---|---|
| Days after administration | 1 | 7 | 14 |
| Administration group | 5.79 | 8.99 | 10.91 |

As seen in Table 6, an almost constant blood concentration was kept for 2 weeks in an administration group receiving the preparation of Example 11.

The sustained-release preparation of the present invention sustainedly releases an anti-endothelin substance, serving well in the treatment of endothelin-associated diseases, particularly chronic complications in diabetes mellitus.

Figure 1:
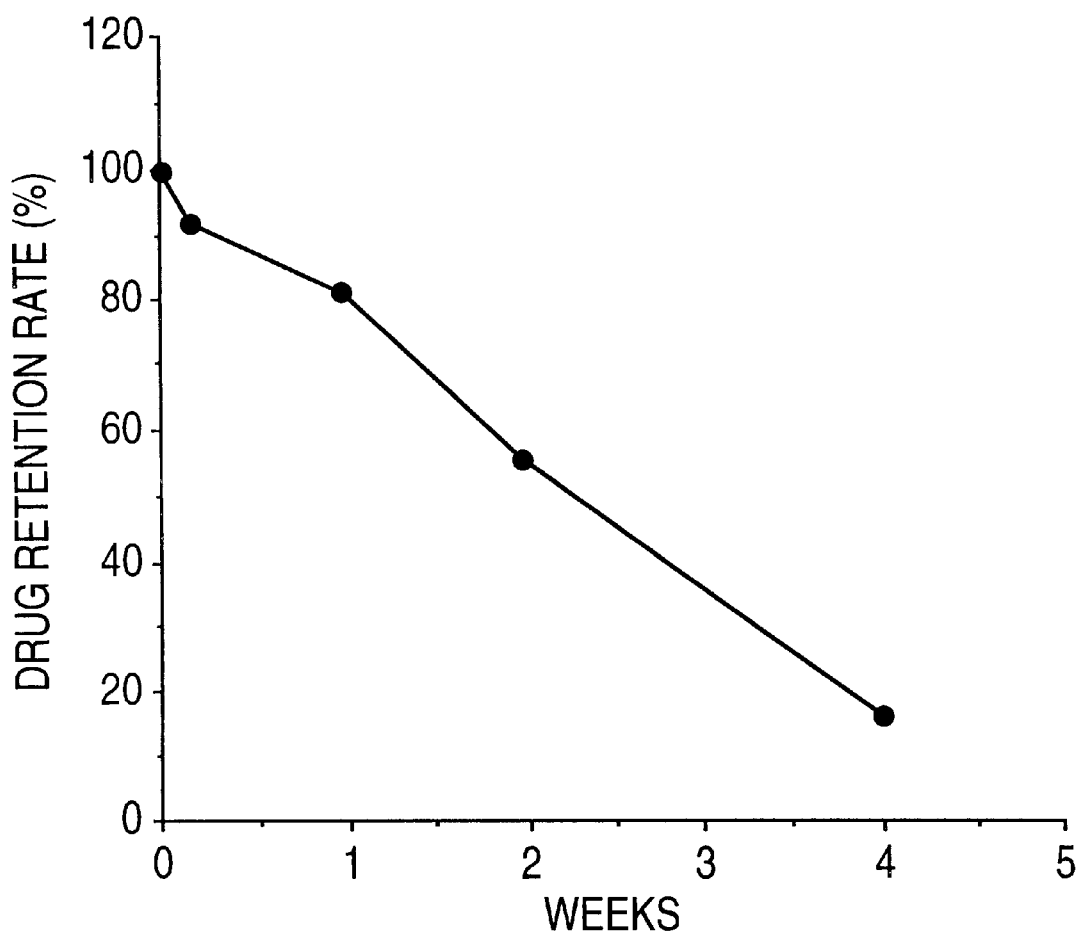
FIG. 1 shows the changes over time in percent drug retention in microcapsules of a sustained-release preparation given to rats, obtained at the site of administration in Experimental Example 1.

We claim:

1. A sustained-release preparation comprising:
   (a) a water-insoluble or slightly water-soluble polyvalent metal salt of a water soluble physiologically active substance comprising a growth hormone, said polyvalent metal salt being formed from a combination comprising a water-soluble physiologically active peptide, derivative or a water-soluble salt thereof and a water-soluble polyvalent metal salt, wherein the solubility of the water-insoluble or slightly water-soluble polyvalent metal salt in water is about 0 to about 0.01% (w/w) at 20° C., and a biodegradable polymer.

2. A preparation of claim 1, wherein the polyvalent metal salt is a transition metal salt.

3. A preparation of claim 1, wherein the polyvalent metal salt is a zinc salt.

4. A preparation of claim 1, which contains about 0.1 to about 50% (w/w) of the polyvalent metal salt.

5. A preparation of claim 1, which contains about 1 to about 30% (w/w) of the polyvalent metal salt.

6. A preparation of claim 1, wherein the biodegradable polymer is an aliphatic polyester.

7. A preparation of claim 6, wherein the aliphatic polyester is a polymer of lactic acid and glycolic acid.

8. A preparation of claim 7, wherein the composition ratio of lactic acid and glycolic acid is 100/0 to about 40/60 (mole %).

9. A preparation of claim 8, wherein the composition ratio is about 90/10 to about 45/55 (mole %).

10. A preparation of claim 7, wherein the weight-average molecular weight of the polymer is about 3,000 to about 20,000.

11. A preparation of claim 7, wherein the weight-average molecular weight of the polymer is about 3,000 to about 14,000.

12. A preparation of claim 6, wherein the aliphatic polyester is a homopolymer of lactic acid.

13. A preparation of claim 12, wherein the weight-average molecular weight of the homopolymer is about 3,000 to about 20,000.

14. A preparation of claim 12, wherein the weight-average molecular weight of the homopolymer is about 3,000 to about 14,000.

15. A preparation of claim 1, wherein the preparation is a microcapsule.

16. A preparation of claim 15, wherein the microcapsule is for injection.

17. A preparation of claim 1, which is injectable.

18. A method for the production of a sustained-release preparation comprising admixing a water-insoluble or slightly water-soluble polyvalent metal salt of a physiologically active substance comprising a growth hormone and a biodegradable polymer, wherein the solubility of the water-insoluble or slightly water-soluble polyvalent metal salt in water is about 0 to about 0.01% (w/w) at 20° C.

19. A method of producing a sustained-release preparation comprising:

dispersing or dissolving a water-insoluble or slightly water-soluble polyvalent metal salt of a water-soluble physiologically active substance comprising a growth hormone in an oil phase comprising a biodegradable polymer to form a solid-in-oil emulsion, said polyvalent metal salt being formed from a combination comprising a water-soluble physiologically active peptide, derivative or a water-soluble salt thereof and a water-soluble polyvalent metal salt, wherein the solubility of the water-insoluble or slightly water soluble polyvalent metal salt in water is about 0 to about 0.01% (w/w) at 20° C., adding the solid-in-oil emulsion to a water-phase to make a solid-in-oil emulsion, and in-water drying the solid-in-oil-in-water emulsion.

20. A preparation according to claim 1, wherein said physiologically active substance has a molecular weight from 200 to 200,000.

21. A sustained release preparation according to claim 1, wherein said growth hormone comprises human growth hormone.

22. A method according to claim 18, wherein said growth hormone comprises human growth hormone.

23. A method according to claim 19, wherein said growth hormone comprises human growth hormone.

* * * * *

UNITED STATES PATENT AND TRADEMARK OFFICE
CERTIFICATE OF CORRECTION

PATENT NO. : 6,087,324
DATED : July 11, 2000
INVENTOR(S) : Yasutatka IGARI, et al.

It is certified that error appears in the above-identified patent and that said Letters Patent is hereby corrected as shown below:

On the cover, listed under "Other Publications":

line 10, delete "U.S. Patent Application No. 071 984,323 of Henry Auer, et"; and insert --U.S. Patent application No. 07/984,323 of Henry Auer, et--;

Column 3, line 4 delete "alihatic" and insert --aliphatic--;

Column 11, line 49 recites "about about" the second occurrence should be deleted;

Column 13, line 1 delete "aicd" and insert --acid--;

Column 21, line 46 delete "hetrocyclyl" and insert --heterocyclyl--;

UNITED STATES PATENT AND TRADEMARK OFFICE
CERTIFICATE OF CORRECTION

PATENT NO. : 6,087,324
DATED : July 11, 2000
INVENTOR(S) : Yasutatka IGARI, et al.

It is certified that error appears in the above-identified patent and that said Letters Patent is hereby corrected as shown below:

Column 54, line 54: delete "peptide" and insert --growth hormone--;

line 59: delete "20°C.," and insert --20°C,--;

Column 56, line 12: delete "peptide" and insert --growth hormone--;

line 20: delete "a solid-in-oil emulsion" and insert --a solid-in-oil-in water emulsion--;

Signed and Sealed this

Seventeenth Day of April, 2001

Attest:

NICHOLAS P. GODICI

*Attesting Officer*       *Acting Director of the United States Patent and Trademark Office*